United States Patent
Banerjee et al.

(10) Patent No.: US 11,733,496 B2
(45) Date of Patent: Aug. 22, 2023

(54) OPTICAL IMAGING SYSTEM WITH ENCAPSULATION AND TETHER

(71) Applicant: OMNISCIENT IMAGING, INC., Tucson, AZ (US)

(72) Inventors: Bhaskar Banerjee, Tucson, AZ (US); Richard Pfisterer, Tucson, AZ (US); John Jameson, El Cerrito, CA (US); Chih-Chiang Chang, Tucson, AZ (US); Haiyong Zhang, Tucson, AZ (US)

(73) Assignee: OMNISCIENT IMAGING, INC., Tucson, AZ (US)

( * ) Notice: Subject to any disclaimer, the term of this patent is extended or adjusted under 35 U.S.C. 154(b) by 0 days.

(21) Appl. No.: 18/124,172

(22) Filed: Mar. 21, 2023

(65) Prior Publication Data

US 2023/0221535 A1    Jul. 13, 2023

Related U.S. Application Data

(63) Continuation of application No. 17/231,050, filed on Apr. 15, 2021, now Pat. No. 11,630,287, and a
(Continued)

(51) Int. Cl.
*G02B 13/06* (2006.01)
*G02B 7/02* (2021.01)
(Continued)

(52) U.S. Cl.
CPC ............ *G02B 13/06* (2013.01); *A61B 1/0016* (2013.01); *A61B 1/00018* (2013.01);
(Continued)

(58) Field of Classification Search
None
See application file for complete search history.

(56) References Cited

U.S. PATENT DOCUMENTS 8,167,506 B2 *  5/2012  Martos ................. G03B 15/00
                                                396/427
8,317,414 B2 * 11/2012  Jones ................. G08B 13/1963
                                                396/427
(Continued)

FOREIGN PATENT DOCUMENTS

CN      20904809 U1    7/2019
WO      2011121532 A1  10/2011

*Primary Examiner* — Clayton E. LaBalle
*Assistant Examiner* — Diana Hancock
(74) *Attorney, Agent, or Firm* — Quarles & Brady LLP; Yakov S. Sidorin

(57) ABSTRACT

A tethered imaging camera encapsulated in a shell lens element of such camera enables viewing from inside and imaging of a biological organ in/from a variety of directions. A portion of camera's optical system together with light source(s) and optical detector mutually cooperated by housing structure inside the shell are moveable/re-orientable within the shell to vary a desired view of the object space without interruption of imaging process. A tether carries electrical but not optical signals to and from the camera and controllable traction cords to move the camera, and a hand-control unit and/or electronic circuitry configured to operate the camera and power its movements. Method(s) of using optical, optoelectronic, and optoelectromechanical sub-systems of the camera.

23 Claims, 13 Drawing Sheets

Related U.S. Application Data continuation of application No. PCT/US2021/027212, filed on Apr. 14, 2021, which is a continuation of application No. PCT/US2021/027212, filed on Apr. 14, 2021.

(51) Int. Cl.
  *G03B 15/02* (2021.01)
  *G03B 37/02* (2021.01)
  *A61B 1/04* (2006.01)
  *A61B 1/06* (2006.01)
  *A61B 1/00* (2006.01)
  *A61B 1/05* (2006.01)

(52) U.S. Cl.
  CPC ...... *A61B 1/00096* (2013.01); *A61B 1/00114* (2013.01); *A61B 1/041* (2013.01); *A61B 1/0655* (2022.02); *A61B 1/0661* (2013.01); *G02B 7/02* (2013.01); *G03B 15/02* (2013.01); *G03B 37/02* (2013.01); *A61B 1/00183* (2013.01); *A61B 1/05* (2013.01); *A61B 1/0676* (2013.01)

(56) References Cited

U.S. PATENT DOCUMENTS

| | | |
|---|---|---|
| 10,401,715 B2 * | 9/2019 | Watanabe .............. H04N 23/51 |
| 2008/0151343 A1 * | 6/2008 | Dunki-Jacobs ........ G02B 5/205 |
| | | 359/205.1 |
| 2008/0167521 A1 * | 7/2008 | Sheetz .............. A61B 1/00096 |
| | | 600/101 |
| 2009/0322864 A1 | 12/2009 | Karasawa |
| 2012/0133729 A1 * | 5/2012 | Strzempko ............ G02B 23/08 |
| | | 348/E7.001 |
| 2012/0243861 A1 * | 9/2012 | Svensson .............. G03B 11/00 |
| | | 359/894 |
| 2020/0271924 A1 * | 8/2020 | Abe ..................... H04N 23/695 |

* cited by examiner

FIG. 5
FIG. 6
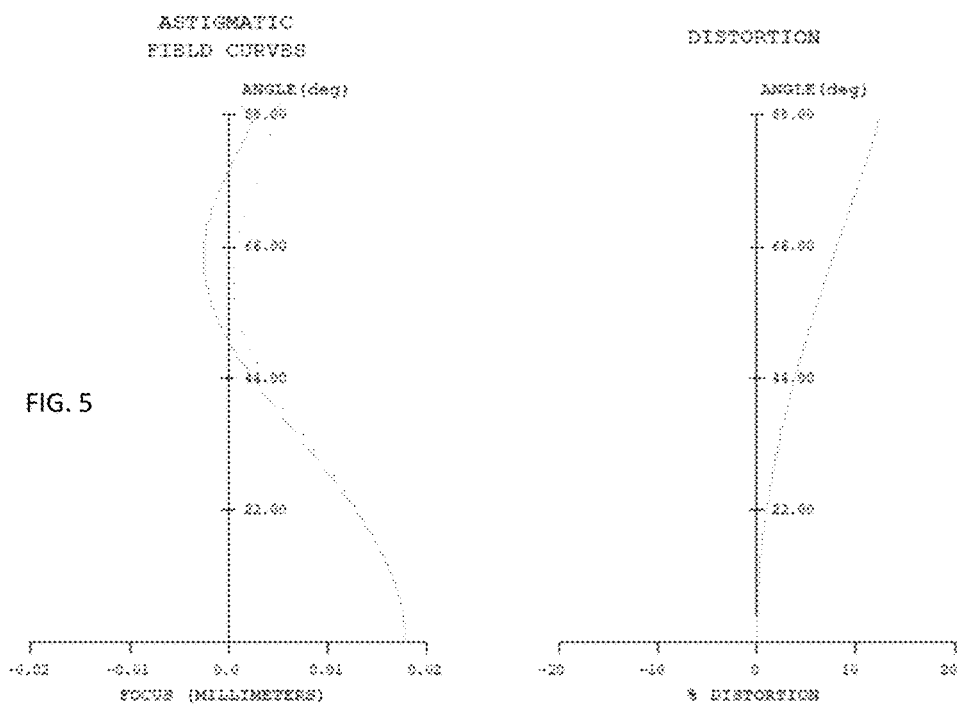
FIG. 7
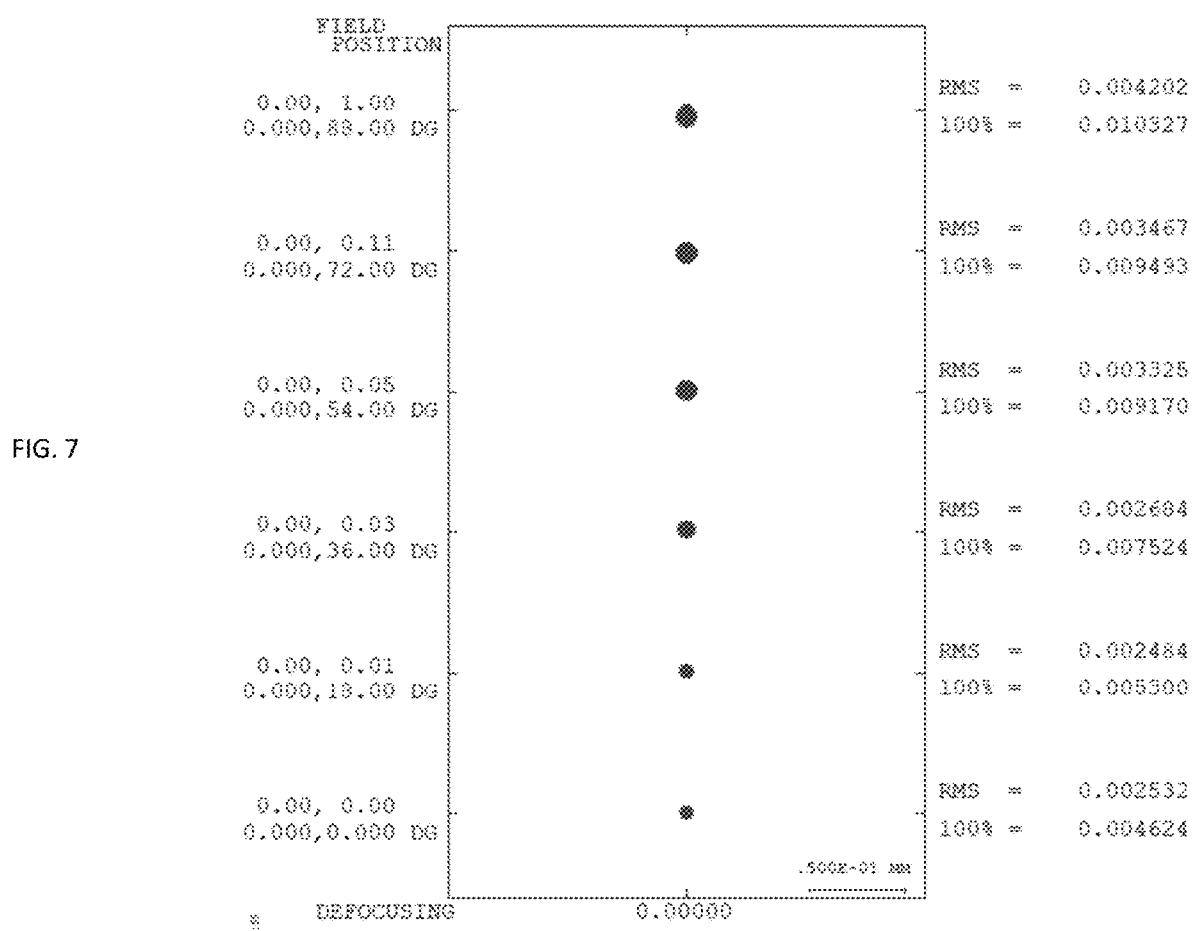

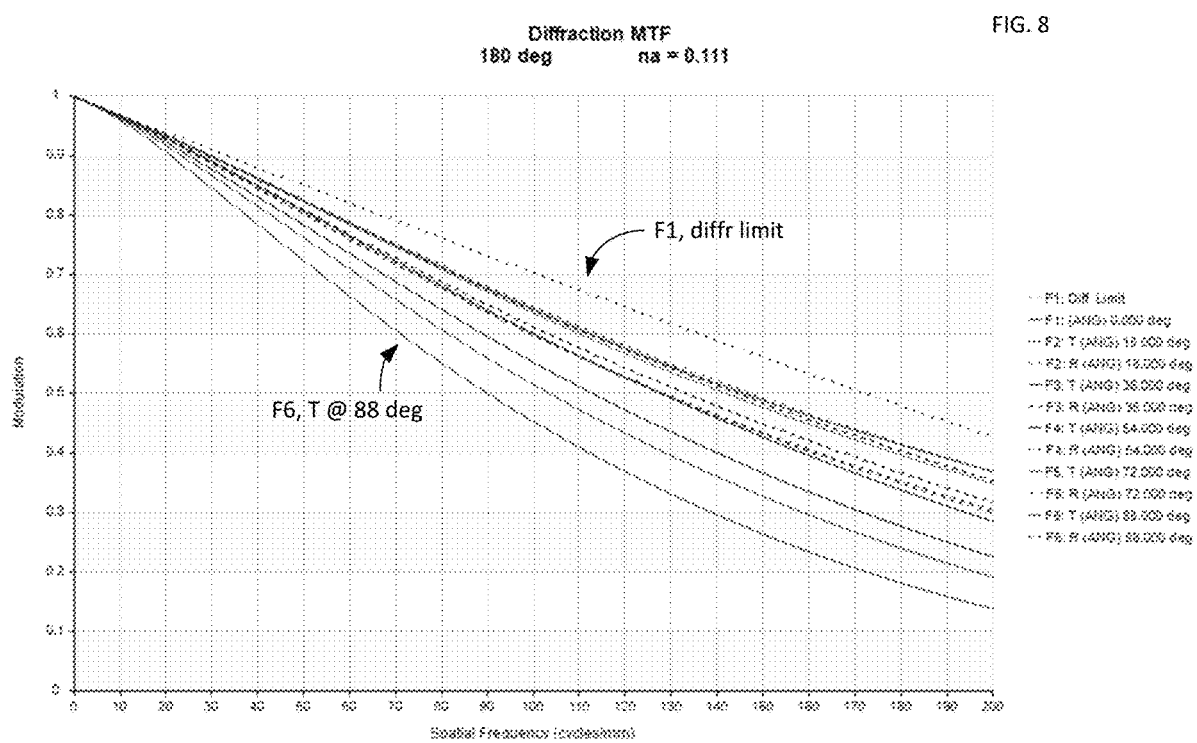
FIG. 8
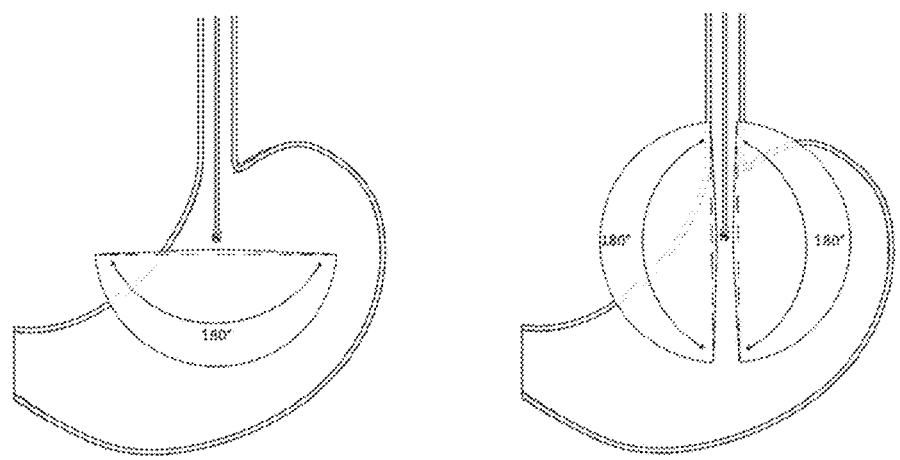
FIG. 9A
FIG. 9B

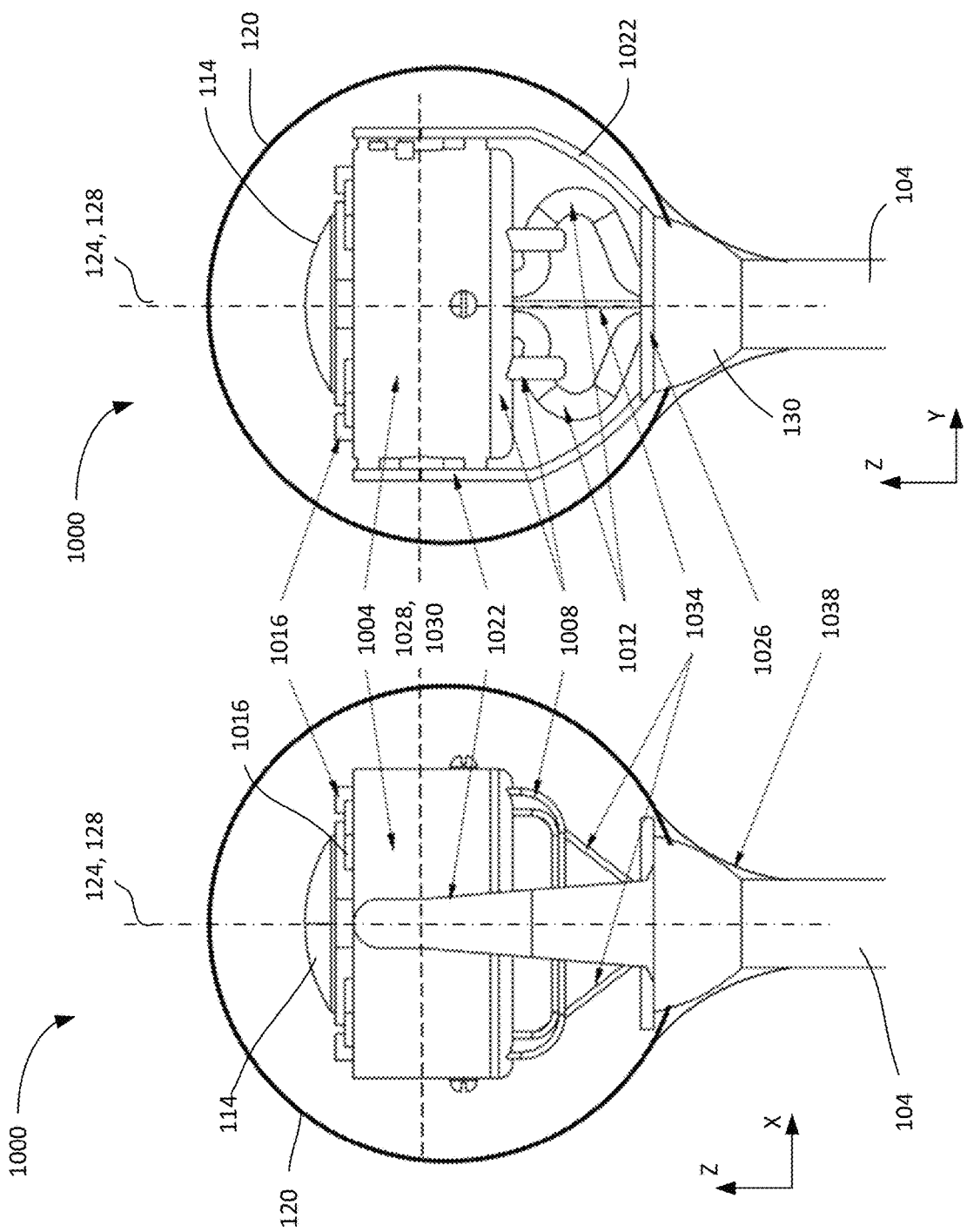

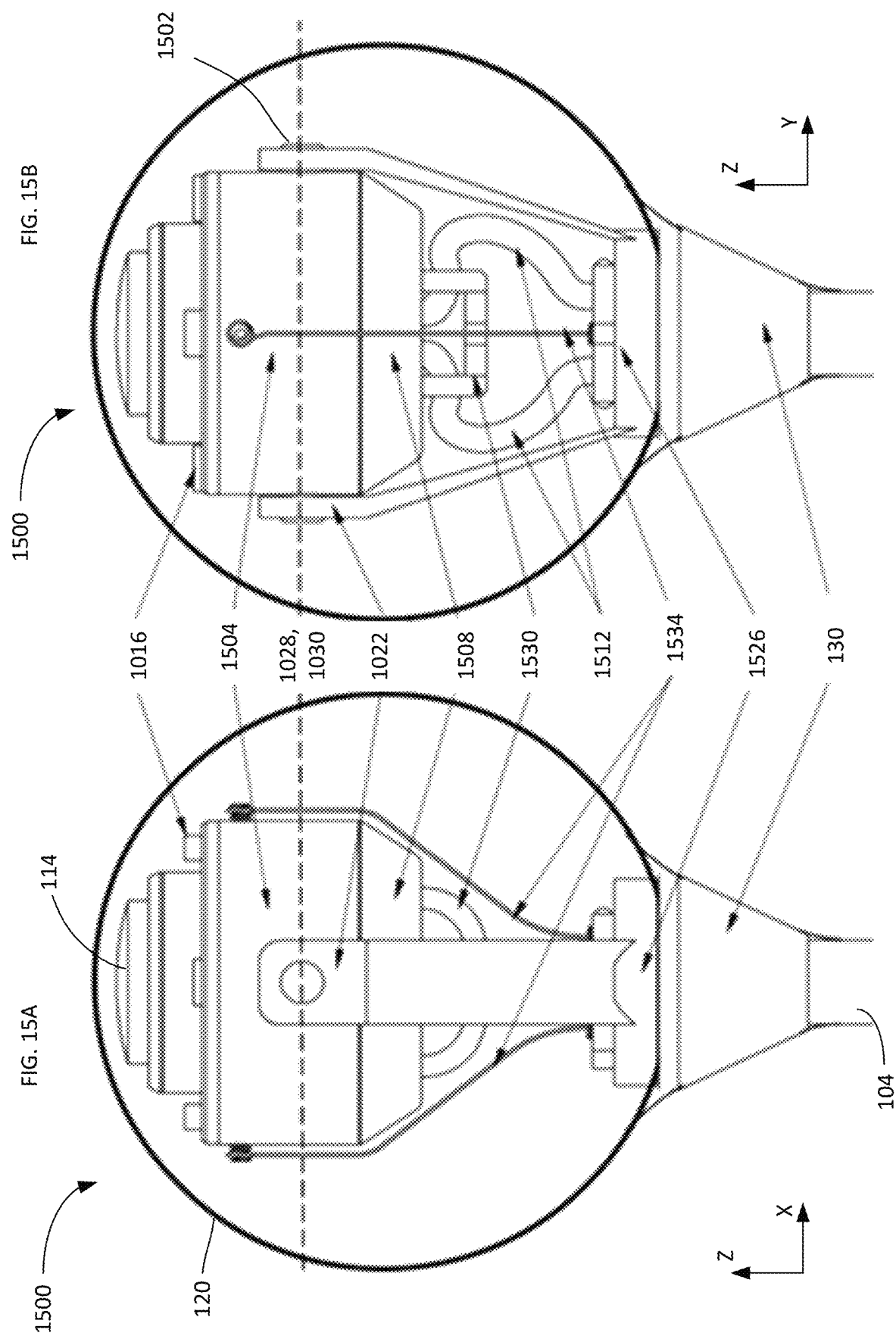

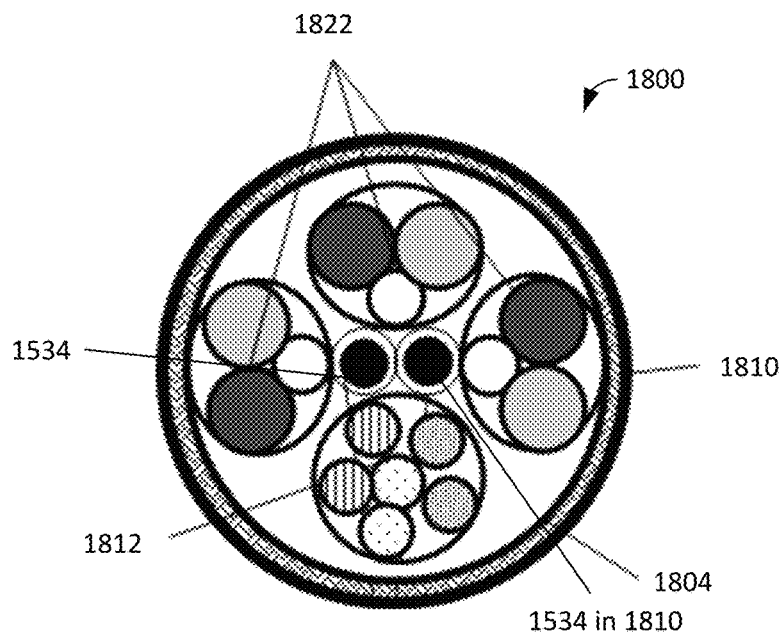
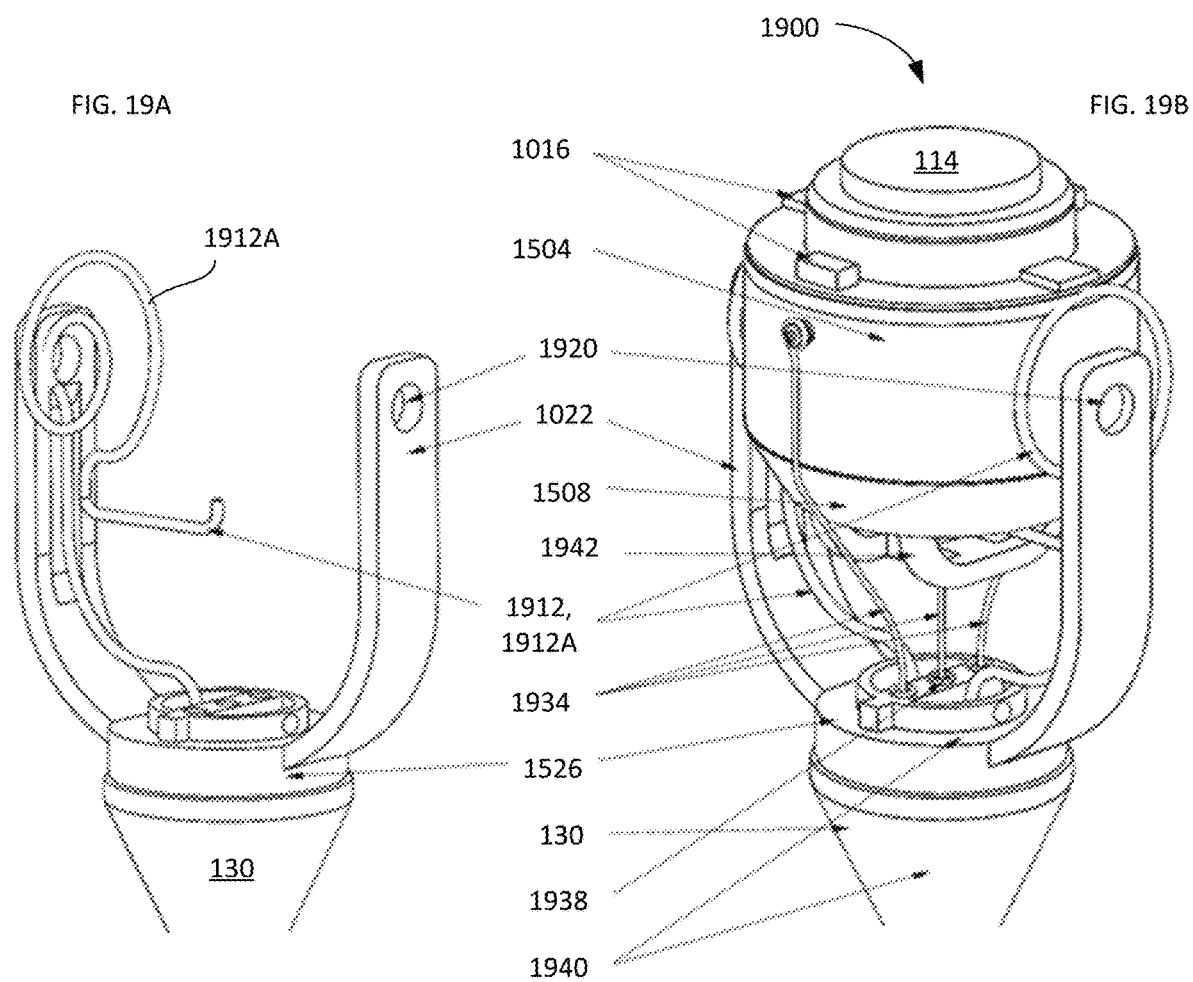

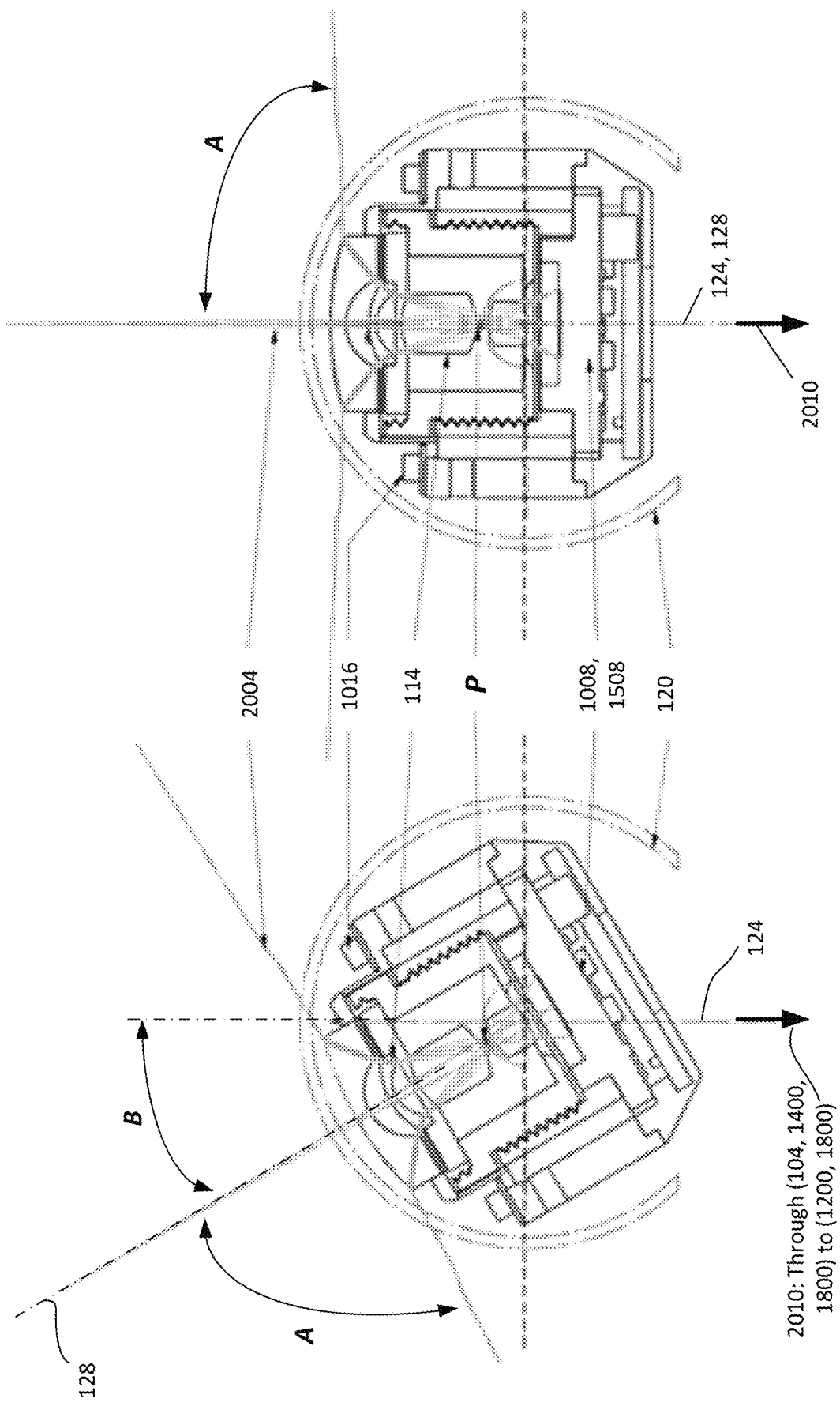

OPTICAL IMAGING SYSTEM WITH ENCAPSULATION AND TETHER

CROSS-REFERENCE TO RELATED APPLICATIONS

This US Patent Application is a continuation of the pending U.S. patent application Ser. No. 17/231,050 filed on Apr. 15, 2021 and now published as US 2022/0334364, which in turn is a continuation of the International Patent Application No. PCT/US2021/027212 filed on Apr. 14, 2021 and now published as WO 2022/220816. This US Patent Application is also a continuation of the International Patent Application No. PCT/US2021/027212 filed on Apr. 14, 2021 and now published as WO 2022/220816. The entire disclosure of each of the above-identified applications is incorporated herein by reference.

TECHNICAL FIELD

The present invention relates to imaging of inside of biological organs and, more particularly, to an imaging system one portion of which is judiciously encapsulated by another portion and is configured to be rotatable within such other encapsulating portion with the use of mechanical members passed through an aperture defined by the encapsulating portion.

RELATED ART

In order to examine specific bodily organs such as the esophagus, stomach or small intestine (gastrointestinal tract), related art currently utilizes endoscopes—elongated, flexible or rigid, instruments configured for imaging internal bodily organs. The structure (and, in particular, the size and shape) of such instruments (about 10 mm in diameter by about 1,100 mm in length) require that examination procedure be formatted in a very specific way: a patient must be at a minimum unperturbed and, preferably, sedated during the procedure. An instrument of such a large size has to be advanced from the mouth, via the pharynx to the esophagus, stomach and beyond by pushing the device forwards while viewing the path along which the device is being moved. At least a portion of such device includes a rigid or flexible long insertion sheath (typically, of about 10 mm in diameter) carrying various wires, optical channels, other hardware components in its hollow and protecting these contents from the environment.

Furthermore, a physician needs to somewhat forcibly advance the endoscope along the digestive tract; the device cannot be simply swallowed and advanced without applying this force. The operation of a so-conventionally-structured scope is then inevitably associated with physical rotation or deviation or bending of, for example, the distal end of the sheath from or with respect to its original position. That, in turn, leads to physical impact between the probe and the physical tissue, thereby causing trauma to the bodily cavity. Even to tolerate such a procedure—let alone to have the examination go smoothly and without disruptions, to collect required data—a patient typically has to be sedated, which increases the risk of a procedure by blunting the protective physiological reflexes. Traditional endoscopes achieve viewing in a plurality of directions by moving/bending the tips of the endoscopes to direct imaging cameras, which can result in trauma to the lining of an organ with which the tip interacts. Moreover, retroflexed views through such traditional endoscopes are at least partially obscured by the very sheath of the device.

While wireless, stand-alone swallowable imaging probes encapsulated in a sealed capsule-like housing could be considered as alternatives to provide images from within the body, such as gastrointestinal tract, the imaging process is recognized to be hampered by poor image resolution due to small optics and a small image sensor used, with images that usually have to be first stored and viewed only after the procedure once downloaded. A skilled artisan readily recognizes that, even if a wireless capsulated camera could be formatted to transmit live video, it would not be practical to implement control of the camera at the discretion of the user because the direction, position, and movement of the wireless capsule is determined by gravity, changes in body position, muscular movements of gastrointestinal organ or surrounding organs—most of which parameters vary with time and from patient to patient. The lack of control of imaging direction, for example, detrimentally affects the imaging procedure as it results in incomplete viewing of an organ cavity (such as the stomach, for example), thereby leading to missed lesions and eventual misdiagnosis. Even if a lesion or target is briefly observed, a free-falling capsule prevents such an area to be imaged a second time or repeatedly, if it is required to reconfirm the collected information or provide a detailed close-up view. Indeed, a physician may require a side view of an ulcer in a stomach to observe its margin in order to assess for signs of neoplastic growth such as raised margins; or may wish to use to use additional monochromatic wavelengths rather than white light, to increase contrast of imaging; or use imaging methods including fluorescence, auto fluorescence, or second- or third-harmonic generation techniques to garner structural or metabolic information about various tissues. The need for repeated views with the same or different imaging modalities and from different angles can provide valuable diagnostic information.

When examining an organ such as the stomach, it is important to repeatably view the entire organ so as not to miss any lesion. The operator's ability to control the rotational movement as well as movement along the altitude as well as the conscious patient's ability to change body positions will allow a completely spherical view to be acquired. A completely spherical view is not ordinarily possible with a traditionally-configured sheathed scope-like probe tube (let alone the complexities involved in carrying out the corresponding imaging procedure), while both the wide-angle and repeatable imaging process cannot be achieved with a stand-alone encapsulated camera. Currently-available imaging methodologies, therefore, fall short of satisfying the specific needs of imaging specific bodily organs such as the esophagus, stomach or small intestine (gastrointestinal tract) at least as far as versatility of the imaging and simplicity of the use are concerned.

SUMMARY

Implementations of the idea of the invention address methods and apparatus for a tethered and encapsulated optoelectronic imaging system structured to view and image—in a repeatable fashion, if required—a target object space in a variety of directions from inside biological organs (such as, for example, the esophagus, stomach or intestines) or from inside inanimate objects or space. A portion of the optical system inside the encapsulating housing or shell is structured to be judiciously repositionable and can be oriented in a variety of directions while the shell—with respect to the considered portion of the optical imaging system itself—remains fixed, thereby allowing the user to obtain a desired view without moving or repositioning the overall tethered system. (And yet, the repositioning of the overall tethered system can be carried out by manipulating the tether, as discussed below.) A portion of the overall imaging camera inside the encapsulating housing shell contains lens elements, an image sensor or optical detector, some illumination sources, and associated electronics as described, all held in a compact housing mechanical structure, and thus can be viewed as an optoelectromechanical system. This camera housing structure is configured in such a way as to be able to move inside the encapsulating shell, as desired by the user, and without any interruption of the imaging process. The narrow, flexible tether (configured such as to facilitate the swallowing of the system by a patient) is affixed to the capsule-like housing and not only carries wiring needed to power the imaging camera and collect and transfer the image data, but also the cords or strings configured to affect the desired movement of a portion of the camera inside the capsule. Notably, in advantageous contradistinction with sheathed portions of conventionally-structured endoscopes (laparoscopes, or other conventional imaging probes), the tether of an embodiment of the invention does not contain (that is, is devoid of, or lacks) any optical channel configured to transmit light from one end of the tether to another. Depending on the specifics of the particular implementation, the shell encapsulating the optical system inside the volume of the shell may be configured as a part of the optical imaging train that is required to be present for forming an optical image of the target object space of operationally-satisfactory quality, thereby causing the shell to be viewed and operated as a lens element itself. In such a specific case, as will be readily appreciated by a skilled person, one portion of the optical imaging train is structured to move inside another portion of the optical imaging train.

Embodiments of the invention provide an optical imaging system that includes at least a first optical element dimensioned as a substantially-spherical shell having a shell axis and an optical lens that has an optical axis and a front lens element, the front lens element having an apex at the optical axis and facing the first lens element. Here, the optical lens is mounted within the first optical element such as to be rotatable about an axis of rotation at a rotation angle that is defined between the shell axis and the optical axis and that can be of each and every value within a range from about −90° to about +90° in a chosen plane containing both the shell axis and the optical axis. When a holder structure, dimensioned to hold elements of the optical lens is fixed spatial orientation with respect to one another, is added to the optical imaging system, the imaging system may include at least one source of light affixed to the holder structure and/or an optical detector affixed to the holder structure. (In this case, the combination of the holder structure, the at least one source of light, and the optical detector are configured to be at least partially enclosed within the first lens element and rotatable synchronously with the optical lens within the first optical element about the axis of rotation.) In at least one case, the optical imaging system includes a tether that is structured to include an electrically-conducting member electrically-connecting one or more of the at least one source of light and the optical detector with an end of the tether distal to the first lens element and, at the same time, not contain any optical member transmitting light along the tether. Optionally but preferably, the optical imaging system includes a traction string within the tether (with a proximal end of the traction string connected to the holder structure to effectuate a rotation of the optical lens about the axis of rotation when repositioned along the tether). Preferably but optionally, the electrically-conducting member is positioned within the first optical element to form a spatial loop about an axle defining the axis of rotation and supporting the holder structure at a stand element that maintains its orientation with respect to the first optical element regardless of the rotation angle. The optical imaging system may be structured in such a way that, when rotation of the optical lens is carried out within the first lens element, the apex of a front lens element of the optical lens remains substantially equidistant from the substantially-spherical shell regardless of a value of the rotation angle within the range of rotation; and/or be structured such as to have a constant field of view regardless of the rotation angle within this range. In one specific case, each of the two lens elements of the optical lens that are closest to the substantially-spherical shell is shaped as an optical meniscus. In at least one implementation, the optical imaging system is configured to dynamically image an object space within a linear angle of at least 350 degrees by scanning such angle with the optical lens having a semi-angular FOV of more than 40 degrees while, at the same time, maintaining an optical surface of the optical imaging system that is closest to the object space in a substantially unchanged orientation and position with respect to the object space.

Embodiments of the invention additionally provide an imaging camera that includes an optical system defined by a first lens element and an optical lens, an optical mount maintaining mutual orientations of lens elements of the optical lens with respect to one another; at least one source of light cooperated with the optical lens in a spatially-fixed orientation with the use of the optical mount, and an optical detector juxtaposed with the optical mount to acquire light from an object space through the first lens element and through the optical lens to form an optical image of the object space. In the provided configuration, the combination of the optical lens, the optical mount, the at least one source of light, and the optical detector are encased by the first lens element and configured to be rotatable within the first lens element about an axle of the optical mount. In at least one specific case, the imaging camera additionally includes an electrically-conducting member drawn through an aperture defined in the first lens element into a volume encased by the first lens element and connected to at least one of the at least one source of light and the optical detector; and/or a string drawn through an aperture (defined in the first lens element) into a volume (that is encased by the first lens element) and connected to the optical mount such that repositioning of the string along a length of the string causes the optical lens rotate within the first optical element about an axle such that a pre-determined point at the optical lens remain substantially equidistant from the first lens element regardless of an angle of rotation of the optical lens.

Embodiments of the invention also provide a method for imaging an object with an optical system comprising a first lens element having a first axis and an optical lens having a second axis. The method includes the steps of rotating the optical lens within a volume defined by the first lens element about an axis of rotation located within the volume; at each angle of so rotating, acquiring light from the object through the optical system with an optical detector positioned within the volume; and transferring a signal representing a spatial distribution of said light from inside the volume lens element to outside of the volume. (In at least one specific case, the step of transferring a signal representing a spatial distribution of the light may include transferring such signal along the tether that is devoid of any optical element, while a distal end of the tether being attached to a component contained within the volume.)

In at least one implementation of the method, at least one of the following conditions is satisfied: (a) the first lens element encases at least a portion of the optical lens, and further comprising irradiating an object with illuminating light delivered from a source of light through only the first lens element, and (b) the process of acquiring includes acquiring the light from the object through both the first lens element and the optical lens; additionally, the process of transferring includes transmitting an electrical signal and is devoid of transmitting an optical signal. Additionally or alternatively, and in at least one implementation, the process of rotating may include rotating the optical lens at a latitude angle of rotation while maintaining a distance (that separates a front lens element of the optical lens from the first lens element) substantially constant for every latitude angle of rotation chosen at least within a range from about +90° to about −90° as measured between the first axis and the second axis in a plane containing both the first axis and the second axis. Additionally or in the alternative, and in at least one implementation of the method, the method may include a step of rotating the first lens element about the first axis by an azimuthal angle of rotation. (In one specific instance case, and when the optical system has a field-of-view with a semi-angle of at least 80°, an aggregate solid viewing angle subtended by the optical system in the object space by the rotation of the optical lens about the axis of rotation and by the rotation of the first lens element about the first axis by 360° is at least 3π steradian.) Notably, the step of rotating the first lens element about the first axis may include twisting a tether that is drawn through an opening in the first lens element to connect contents of the volume with a point outside the first lens element, while the tether lacks any optical channel connecting first and second points along a length of the tether.

In at least one specific implementation of the method, the first lens element is dimensioned as a substantially-spherical shell having an aperture subtending a solid angle not exceeding 0.6π steradian as viewed from a center of curvature of a surface of the first lens element, while the process of transferring a signal representing a spatial distribution of light includes transferring an electrical signal through such aperture in the first lens element. In at least one specific implementation, the distance separating the front lens element of the optical lens from the first lens element is maintained constant during the process of rotating the optical lens within the volume while, at the at the same time, the method is devoid of (does not include) a step of repositioning the axis of rotation within the volume. In at least one implementation, the process of imaging includes imaging a target portion of an esophagus, while the method additionally includes a step of swallowing the optical system by a patient. (Here, the first lens element is structured as a substantially-spherical shell having an aperture therein dimensioned to provide access to the volume, and such aperture is substantially fluidly-impenetrably sealed with a stress-relief seal.)

In at least one implementation, the step of acquiring light from the object through the optical system includes acquiring such light through a sequence of three meniscus lens elements and/or acquiring such light through a sequence of two lens elements, each having a corresponding positive optical power and/or acquiring such light through a stop aperture that is separated from the object by a first optical group including three lens elements and from an image plane by a second optical group that includes two lens elements. The step of acquiring includes transmitting the light through a lenslet from the first optical group and through a lenslet from the second optical group, such lenslets having respective optical powers of opposite signs.) Alternatively or in addition, every lens element from the first optical group has a corresponding optical power with a first sign, and every lens element from the second optical group has a corresponding optical power with a second sign, the first sign being opposite to the second sign.

In implementing the method, the optical system may be configured to have a FOV with a semi-angle exceeding 80°, while an aggregate, overall FOV that the optical system covers in object space as a result of rotating the optical lens has a semi-angle of at least 170° with respect to the first axis. Alternatively or in addition, the method may comprise repositioning the object with respect of the optical system.

BRIEF DESCRIPTION OF THE DRAWINGS

The invention will be more fully understood by referring to the following Detailed Description of Specific Embodiments in conjunction with the not-to scale Drawings, of which:

FIGS. 5, 6, and 7 respectively illustrate field curves, distortion characteristics, and the spot diagrams associated with the practical use of the embodiment of FIG. 3 during imaging of the object space in the corresponding FOV.

FIG. 8 presents the curves of the modulated transfer function (versus imaging field) for the embodiment of FIG. 3.

FIGS. 9A, 9B illustrate schematically viewing of a bodily organ with the encapsulated embodiment of the invention depending on the angular position of a portion of the optical system of the imaging camera.

FIGS. 10A, 10B illustrate, in side views, an embodiment of a portion of the imaging camera schematically showing at least portions of tilt-driving cords/strings and electrical cables/members/wires inside the housing shell. The tilt motion is driven by two lateral cords and dampened by a third cord. FIG. 10A: a side view showing 'posts'; FIG. 10B: a front view showing the center cord.

FIGS. 15A, 15B illustrate, in side views, a related embodiment of the system of the invention schematically showing at least portions of tilt-driving cords/strings and electrical cables/members/wires inside the housing shell, as configured in this embodiment. The tilt motion is driven by two lateral cords/strings attached to an outside surface of the housing of the lens. A third, dampening cord/string, is optional and is not shown. FIG. 15A: a side view showing 'posts' and both of the tilt cords; FIG. 15B: a front view showing only one of the cords.

FIG. 18 illustrates schematically a cross-section of an embodiment of a tether with electrically-conducting members and spiral coils containing cords/strings for traction drawn through the tether, configured with the use of the embodiments of FIGS. 15A through 17.

FIGS. 19A, 19B schematically illustrate yet another related embodiment, in which at least one of the electrical members/wires (connecting the optoelectronic system of the camera with an outside, external point and drawn through the tether) is directed laterally to form a spiral loop about the axle of rotation of the camera before passing through corresponding hole(s) ion the base plate and entering the tether. The presence of the spiral loop(s) facilitates the tilt of the camera repeatedly without breaking the electrical wires. The loops may be formed on one of both axels present in the embodiment.

FIGS. 20A, 20B illustrate is a simplified cross-section views an embodiment of the imaging camera of the invention in two positions. FIG. 20A: nominal mutual orientation between the outer lens element and a portion of the camera enclosed by the outer lens element. FIG. 20B: the portion of the camera enclosed by the outer lens element is rotated at a predetermined angle B with respect to the outer lens element.

Figure 1:
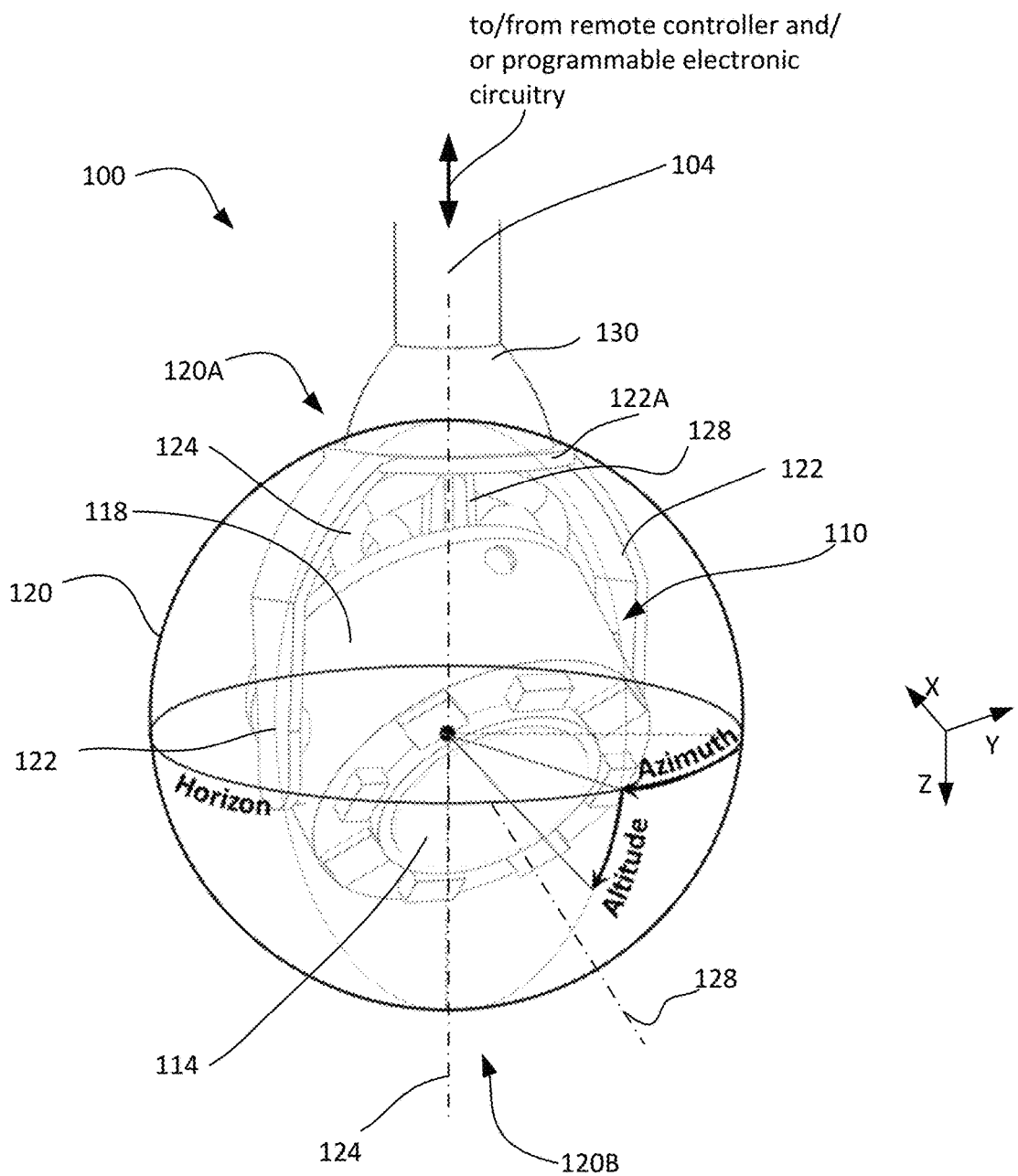
FIG. 1 provides a schematic perspective view of a portion of an embodiment of the invention.

Generally, the sizes and relative scales of elements in Drawings may be set to be different from actual ones to appropriately facilitate simplicity, clarity, and understanding of the Drawings. For the same reason, not all elements present in one Drawing may necessarily be shown in another.

DETAILED DESCRIPTION

In accordance with preferred embodiments of the present invention, methods and apparatus are disclosed for a camera structured as a tethered capsule and configured for imaging the inside(s) of hollow biological organs.

The much smaller dimensions of a tethered capsule (a sphere-like body of about 10 mm in diameter with a slim, flexible tether of about 3 mm of a cross-sectional extent) not only allows the examination to be tolerated without sedation, but requires the patient to be awake and cooperate by swallowing the capsule, to help to advance the capsule from the mouth to the stomach or the small intestine. Indeed, the size and flexibility of the utilized tether makes it practically impossible to advance the capsule into a bodily organ by force.

However, once swallowed, the variety of directions a tethered capsule can view is limited. The advantage of a capsule with operator-directed robotic movement of the camera(s) inside the capsule is to enable a plurality of views without requiring the capsule itself to be redirected. The tethered capsule, however, enables viewing of an organ or inanimate space that are beyond the capabilities of a wireless capsule with stationary cameras. The viewing ability of such a an embodiment approaches, indeed surpasses that of a traditional endoscope; its small volume and flexibility not only allows an organ to be viewed without sedation and with greater safety, but allows variable directions of views to be obtained, without bending or changing the shape and/or position of the embodiment.

By confining movements of a portion of the optical imaging system within the outer shell or capsule of the overall camera, trauma to the lining of an organ during a viewing process (something that often occurs during traditional endoscopy when the tip of the endoscope is redirected to change the angle of view) is avoided. Moreover, retroflexed views during traditional endoscopy are partially obstructed by the insertion tubes of endoscopes (about 10 mm in diameter), whereas the view obstructed by a slim tether will be negligible and easily compensated by movements of the organ, space or organ, allowing a completely spherical view to be obtained. In an inanimate space, such a tethered capsule with robotic-eye camera(s) allows viewing to be obtained in multiple directions through narrow orifices and in small areas where a traditional borescope does not have the room to flex its distal end.

The tethered capsule with a portion of the optical system of the invention moveable inside the capsule provides the versatility of observing the object space in different directions without requiring the capsule itself to be oriented in different directions. The implementation of the proposed embodiment achieves the change of viewing directions, comparable to that provided by an endoscope, while not reorienting the orientation of the capsule in the object space, but by movement of the optical lens inside the capsule. The tethered encapsulated implementation of the idea of the invention, therefore, provides the viewing coverage comparable and/or exceeding that of an endoscope while remaining at a fraction of the endoscope size, enabling the viewing procedures to be performed without sedation and with greater safety.

Overview of an Encapsulated System

In accordance with an idea of the invention, with reference to FIG. 1 that provides a general schematic view of one embodiment, a system 100 is structured as a tethered (104) optoelectronic system 110 (configured as at least a portion of an imaging camera and containing at least an optical lens 114 in an optical lens holder structure 118). A The imaging camera 110 is held by camera stands 122 merging to a supporting base plate 122A inside an optically-transparent housing shell or capsule 120 such as to remain moveable within the shell at least about an axis of rotation (which is defined with respect to the stands 122 and/or axle(s) of rotation which may be connecting the stands 122 with the holder 118, and which may be represented by the angular coordinate denoted as "altitude", and which in FIG. 1 corresponds to the Y-axis of the local system of coordinates). The holder 118 of the optical lens 114 in conjunction with at least the supporting stands 122 and the supporting base plate 122A may be considered and interchangeably referred to as a camera housing structure. The optoelectronic and mechanical components of the imaging camera of the embodiment are operationally and physically connected with a point outside the shell 120 and at a distal point of the tether 104 at least with electrically-conducting member(s) 124 and mechanical cords or strings 128 passing through the tether as discussed elsewhere in this disclosure. Notably, the camera housing structure is configured within the shell 120.

The capsule/shell 120 is smooth-surfaced, rounded at least at its proximal and distal ends 120A, 120B to allow easy swallowing of the capsule 120 by a human and removal of the shell with its contents from the body with the use of the tether 104. Nominally, the capsule 120 is spherical in shape. The size and dimensions (of about 10 mm diameter) of the shell 120 facilitate the use of muscles of swallowing whereby peristalsis is used to advance the swallowed capsule 120 along the lumen of the esophagus and enter the stomach (similarly to how swallowed food reaches the stomach). In practical use of the embodiment 100, peristalsis can be used to advance the embodiment beyond the stomach or in another part of the body entered through a natural orifice or stoma. A skilled artisan will readily appreciate that a much smaller capsule (e.g. the one with less than 3 mm diametrical dimension) cannot be so easily swallowed and advanced through the esophagus; furthermore, at such small a size, the internal to the housing shell optics has to be so small as, when practically implemented, not be able to provide high-resolution images—unlike a system 100 sized to containing a larger imaging sensor (optical detector) as part of the camera 110.

At least the portion of the outer casing 120 of the embodiment 100, through which imaging of the target object space is carried out, is substantially spherical, optically-transparent and of optical quality as understood by a skilled artisan and preferably of uniform thickness, and watertight (fluidly sealed), thereby allowing the optical images of an object space outside the shell 120 to be captured clearly and without distortion through and with the functional, optical-imaging-wise participation of such outer shell 120. It is understood, therefore, that in an optional but preferred implementation the optical system of the imaging camera of the invention includes and requires the presence of the shell 120 that is dimensioned as a lens element having a non-zero optical power. In this case, understandably, the camera housing structure is configured within a non-zero optical power lens element forming a portion of the optical system of the very camera that such housing structure supports, and a portion of the imaging camera is encapsulated in such lens element forming a portion of the optical system of the very imaging camera, and electrical and mechanical members 124, 128 in this case are passing into the tether 104 through an aperture defined in such lens element.

At this point, defining the meanings of at least several terms would be beneficial. To this end, for the purposes of this disclosure and appended claims—and unless specifically defined otherwise, a "spherical shell" is defined as and considered to be a region of a ball between two concentric spheres of different radii. (In that sense, a skilled artisan will understand that a spherical shell is a generalization of an annulus to three dimensions.) A "substantially spherical shell" is defined as an approximation to the spherical shell in that the bodies limiting the substantially spherical shell are substantially spherical or substantially spheres—that is, certain dimensional deviations from the ideal spherical surface shapes (which are typical during the formation of manufacturing of a sphere or a spherical surface and/or which are defined by the variation of radii of such spheres within the range of +/−20% of the nominal radii values, preferably within the range of +/−10% of the nominal radii values, even more preferably within the range of +/−5% of the nominal radii values, and most preferably within the range of +/−2% of the nominal radii values) are allowed and remain within the scope of the claims. In addition or alternatively, and optionally, the concentricity of such substantially spheres limiting the substantially spherical shell may not be perfect, but may be frustrated in that the distance separating the nominal centers of the two substantially-spherical bodies limiting the substantially-spherical shell may be between zero and 20% of the largest value of the radii of these two bodies, preferably not exceed 10% of such largest value, more preferably not exceed 5% of such largest value, and most preferably not exceed 2% of such largest value. In the ideal case, the substantially spherical shell has a thickness the value of which remains constant as a function of angle measured with respect to a chosen axis passing the spatially-coincident centers of the two concentric spheres of different radii limiting and defining such substantially spherical shell.

Similarly, as used in this application and unless expressly defined otherwise, the terms "lenslet" and "lens element" are defined to refer to a single, simple, structurally-indivisible and used singly optical component bound—in a direction of the axis of such component—by two optical surfaces that changes the degree of convergence (or divergence, or collimation) of light passing through or traversing such component. In comparison, the terms "lens", "group of lenses", "lens system" and similar terms are defined to refer to a combination or grouping of lenslets or lens elements. Here, the optical doublet, for example, which is made up of two simple lenslets or lens elements paired together, is referred to as a lens and not as a lens element.

The term "image" is generally defined as and refers to an ordered representation of detector output corresponding to spatial positions. For example, a visual image may be formed, in response to a pattern of light detected by an optical detector, on a display device X such as a video screen or printer. A "real-time" performance of a system is understood as performance that is subject to operational deadlines from a given event to a system's response to that event. For example, a real-time extraction of imaging information (such as a spatial distribution of optical irradiance, for example) from an optical detector of an imaging camera device may be one triggered by the user or a microprocessor programmed to do so and executed simultaneously with and without interruption of a process of optical image acquisition during which such spatial distribution has been detected.

The term "object space" is conventionally defined and understood as the space located outside of the optical imaging system in question and a portion of which—referred to as an object—is imaged through the optical imaging system onto an image surface (which may substantially coincide with a surface of tan optical detector). An object point and its image, formed with the use of the optical imaging system, are considered to be optically-conjugate to one another.

The term "optically-conjugate" and related terms are understood as being defined by the principal of optical reversibility (according to which light rays will travel along the originating path if the direction of propagation of light is reversed). Accordingly, these terms, as referring to two surfaces, are defined by two surfaces the points of which are imaged one on to another with a given optical system. If an object is moved to the point occupied by its image, then the moved object's new image will appear at the point where the object originated. The points that span optically-conjugate surfaces are referred to and defined as optically-conjugate points.

Now, referring again to FIG. 1, a nominal mutual orientation (or, nominal orientation, for short) between the substantially-spherical shell or dome 120 and an optical lens 114 housed within such shell or dome is defined when the shell axis 124 (or axis of the shell passing through the center of the substantially-spherical shell) and an optical axis 128 of the optical lens 114 substantially coincide (that is, when the angle between these two axes is substantially zero). In the orientation illustrated in the example FIG. 1, the axes 124, 128 are shown inclined with respect to one another.

Depending on the specific implementation, the substantially spherical surface(s) of the domes or shell 120 (about 10 mm in outer diameter) can be diamond-turned or injection-molded and made from transparent plastic, such as Polymethyl methacrylate (PMMA). It can also be made of glass or other appropriate biologically-inert optically-transparent materials. In one case, it has a thickness of about 0.5 mm.

The portion(s) of the casing 120 not used for viewing of the target object space (such as that close to the tether 104) may be made of other, not necessarily optically-transparent materials, and/or does not have to be substantially spherical, and only configured to allow for movement or positioning of the components within the casing. To allow various components an d sub-system of the camera 120 to be assembled inside the housing shell 120, the shell can be made from two or more parts that are joined together after the assembly so that the edges fit snugly and are sealed by water-resistant, clear sealants to secure a smooth surface at appropriate junctions, thereby allowing the assembled embodiments to be fluidly-sealed with the entire surface lending itself to be cleaned and disinfected using approved cleaning and disinfecting procedures. There may be incorporated a strain-relief element 130 between the tether 104 and the shell 120.

Figure 2:
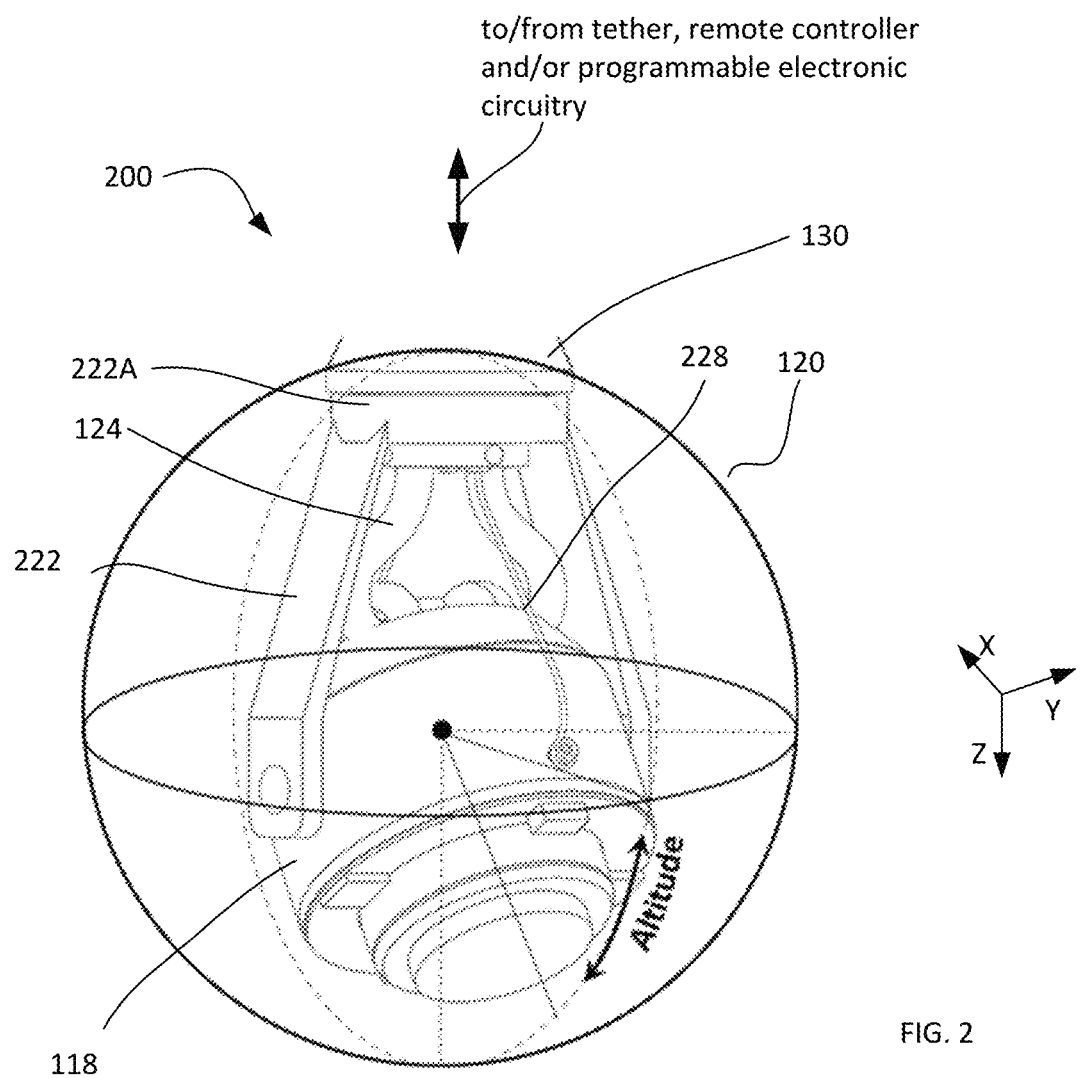
FIG. 2 is a schematic perspective view of a portion of a related embodiment of the invention.
Figure 3:
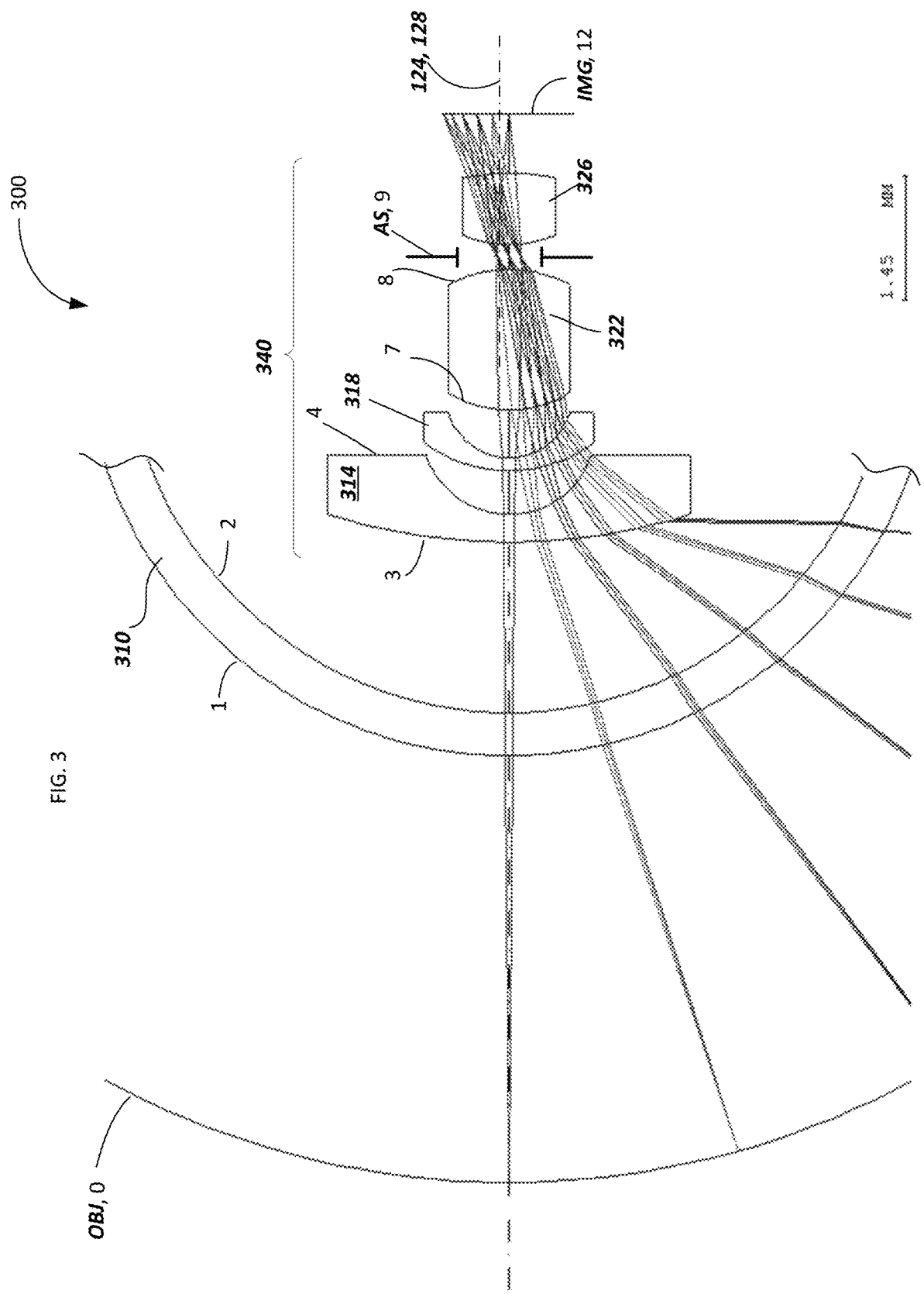
FIG. 3 provides an illustration of an implementation of a train of an optical system of the imaging camera of an embodiment of the invention, configured to image a portion of the object space covered by the corresponding field of view (FOV).

FIG. 2 is a schematic illustration of a related (but not mutually-exclusive with respect to the embodiment 100) embodiment 200 of a portion of the invention, in which the stands 222 and the base plate 222A are shown to be structured a bit differently, while proximal end(s) of the mechanical string(s) or cord(s) 228 is/are affixed to an outer surface of the lens holder 118 (and not to a structural feature inside the holder 118, as is implied in FIG. 1).

Example of an Optical System of an Embodiment of the Imaging Camera

FIGS. 3 through 8 and Table 1 (summarizing an output from the Code V optical design software) provide illustrations to a non-limiting but specific example of an optical imaging system 300 utilized in an embodiment of the invention. A person of ordinary skill in the art will appreciate that, while the optical imaging system of the camera at hand may be, under certain circumstances, configured such that only the optical lens 114 is utilized to form optical image(s) of the target portion of the object space while the optical properties of the shell 120 are not considered in formation of such image(s), in the practically-preferred configuration the optical (imaging) properties of the ever-present optically-transparent shell-shaped capsule should be taken into account as those of a portion of the functional optical imaging system. It is this preferred example that is considered below.

TABLE 1

| ELEMENT | RADIUS OF CURVATURE | | | APERTURE DIAMETER | | |
|---|---|---|---|---|---|---|
| NUMBER | FRONT | BACK | THICKNESS | FRONT | BACK | MATERIAL |
| OBJECT (OBJ) | 10.0000 | | 10.0000 | | | AIR |
| | | | | 140.1046 | | |
| | | | −5.0000 | | | |
| (310) | 5.0000 CX | 4.5000 CC | 0.5000 | 9.8000 | 8.8000 | ACRYLIC |
| | | | 1.0000 | | | |
| | DECENTER(1) | | | | | |
| | | | | 425.9036 | | |
| | | | −2.5000 | | | |
| (314) | 7.1495 CX | 1.0273 CC | 0.3240 | 3.8810 | 1.9490 | NSK16 Schott |
| | | | 0.5148 | | | |
| (318) | 1.6779 CX | 0.7401 CC | 0.1500 | 1.8207 | 1.3530 | NLAF2 Schott |
| | | | 0.5617 | | | |
| (322) | 1.3853 CX | −1.5475 CX | 1.6419 | 1.3046 | 0.5378 | NBASF64 Schott |
| | | | 0.1570 | | | |
| APERTURE STOP (AS) | | | | 0.2776 | | |
| | | | 0.1348 | | | |
| (326) | 1.3363 CX | −2.5708 CX | 0.8360 | 0.4912 | 0.9771 | NFK5 Schott |
| (IMAGE DISTANCE = | | | 0.6864) | | | |
| IMAGE (IMJ) | | INF | | 1.5448 | | |

NOTES:
Positive radius indicates the center of curvature is to the right; Negative radius indicates the center of curvature is to the left; Dimensions are given in millimeters; Thickness is axial distance to next surface; Image diameter shown above is a paraxial value, it is not a ray traced value; Other glass suppliers can be used if their materials are functionally equivalent to the extent needed by the design;

TABLE 1-continued

DECENTERING CONSTANTS

| DECENTER | X | Y | Z | ALPHA | BETA | GAMMA |
|---|---|---|---|---|---|---|
| D(1) | 0.0000 | 0.0000 | 3.5000 | 0.0000 | 0.0000 | 0.0000 |

A decenter defines a new coordinate system (displaced and/or rotated), in which subsequent surfaces are defined. Surfaces following a decenter are aligned on the local mechanical axis (z-axis) of the new coordinate system. The new mechanical axis remains in use until changed by another decenter. The order in which displacements and tilts are applied on a given surface is specified using different decenter types and these generate different new coordinate systems; those used here are explained below. Alpha, beta, and gamma are in degrees.

DECENTERING CONSTANT KEY:

| TYPE | TRAILING CODE | ORDER OF APPLICATION |
|---|---|---|
| DECENTER | | DISPLACE (X, Y, Z) |
| | | TILT (ALPHA, BETA, GAMMA) |
| | | REFRACT AT SURFACE |
| | | THICKNESS TO NEXT SURFACE |

REFERENCE WAVELENGTH = 525.0 NM
SPECTRAL REGION = 450.0-600.0 NM

INFINITE CONJUGATES

EFL = 0.6061
BFL = 0.6606
FFL = −1.5775
F/NO = 4.3708
AT USED CONJUGATES

REDUCTION = 0.0720
FINITE F/NO = 4.5005
OBJECT DIST = 10.0000
TOTAL TRACK = 12.5066
IMAGE DIST = 0.6864
OAL = 1.8202
PARAXIAL

IMAGE HT = 0.6956
IMAGE DIST = 0.7042
SEMI-FIELD

ANGLE = 88.0000
ENTR PUPIL

DIAMETER = 0.1387
DISTANCE = −1.3280
EXIT PUPIL

DIAMETER = 0.3368
DISTANCE = −0.8115

NOTES:
FFL is measured from the first surface; BFL is measured from the last surface As shown in Table 1 and FIG. 3, numbering of the optical elements and optical surfaces is specific to this example of the design. Thus, the object (OBJ) corresponds to the zeroth surface; the optical element 310 representing a portion of the shell-like encapsulating element 120 of FIGS. 1, 2 is bound, along the axis 124, by the surfaces 1 and 2; the following sequence 340 of optical elements 314, 318, 322, and 326 defines an embodiment of the optical lens marked as 114 in FIGS. 1, 2, with the element 314 axially by surfaces 3 and 4, element 318 axially limited with surfaces 5 and 6 (not labelled for simplicity of illustration), element 322 axially limited with surfaces 7 and 8, and element 326 axially limited with surfaces 10 and 11 (not labelled). The aperture stop AS corresponds to surface 9, while the image surface is surface 12. The optical lent 340 and the shell 310 are shown in a nominal mutual orientation.

Light within the range of angles of the FOV of the system 300 arrives from the object OBJ to the outer surface 1 of the shell 310, is optically imaged through the shell 310 and the optical lens 240 (while passing through the aperture stop AS) into the surface 12 to form a spatial distribution of light that is optically-conjugate to the distribution of light at the object—that is, the optical image of the object. The front group of lenslets of the optical lens 240 is formed by the elements 214, 218 each of which in this example is a meniscus lens element, while the optical power of each of the lenslets from the rear group of lenslets of the optical lens 240 (which rear group is separated from the front group of lenslets by the aperture stop AA) has a sign that is opposite to the sign of an optical power of any of the lens elements from the front group. The aggregate FOV of the lens assembly 300 (formed by three meniscus lens elements and two double-convex lens elements in this example) has a semi-angle of 88 degrees and imaging resolution of about 50 µm in a direction transverse to the local axis of the lens 240. (The person of skill will appreciate options of re-design of this example to provide for a different FOV the semi-angle of which generally exceeds 80 degrees, but may be smaller that this value is required.)

The maximum diametrical extent of the lens system 240 does not exceed 4 mm. Material for the lens elements (providing the well-corrected imaging within the spectral bandwidth from about 450 nm to about 650 nm) are summarized in Table 2. The optical detector is configured to acquire an image with image height of at least 1.54 mm. For the purposes of this design, the object space viewed in the FOV of the system 300 was considered to be a spherical surface centered on the axis 128 at located at the object distance of about 10 mm.

Figure 4:
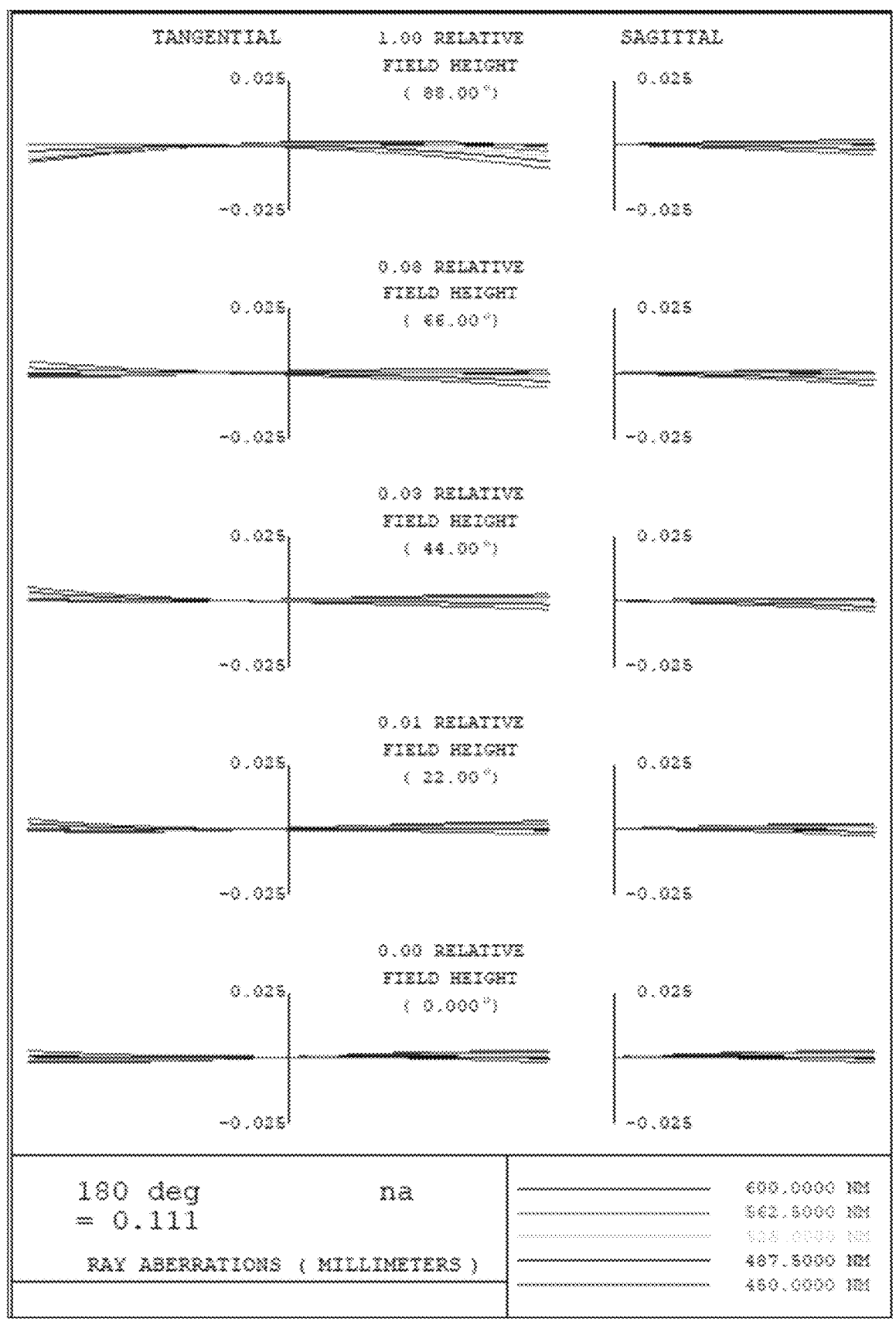
FIG. 4 provides description of transverse ray aberrations during the optical imaging in the FOV through the optical system of FIG. 3.

FIG. 4 illustrates transverse ray aberrations (both in tangential and sagittal planes) representing optical performance of the embodiment 300: the skilled person will readily appreciate that these aberrations are substantially below 12 microns for any field up to at least 88 degrees. FIGS. 5, 6, and 7 illustrate the corresponding spot diagrams and the astigmatic field curvature and distortion as a function of field angle. The optical system is characterized by astigmatism that, in either of sagittal or tangential planes, does not exceed 20 microns at every field height within a field-of-view of the optical system; by the optical distortion that does not exceed 10% at every field angle up to 66°; and by the optical distortion that does not exceed 15% at every field angle up to 88°. The spot diagrams boast the rms spot size below about 4.5 microns at the full field height (field of 88 degrees) and below 2.5 microns at the full file height of up to 18 degrees, and about 2.5 microns for imaging the axial portion of the object in the specified FOV.

For assessing other types of aberrations, the identification of what is practically acceptable comes down to the modulated transfer function (MTF) curves. Based on the proposed design and in reference to FIG. 8 (that illustrates parameters of the MTF characterizing the operation of the embodiment 300 in the visible portion of the spectrum in the aggregate FOV), the ideal solution is substantially close to being diffraction-limited (the top curve among the MTF curves). Notably, the performance of the design on-axis is close to the ideal solution, with some falloff at the edge of the field—and would be considered practically acceptable by a person of ordinary skill in the art in visual and/or photographic optical systems. Specifically, the cut-off frequency of operation in the visible portion of the spectrum is substantially above 200 cycles/mm (both for imaging in tangential and sagittal planes) for imaging in either plane at any field up to at least 88 degrees. Such consideration, accepted in related art, at least in part is explained by the specifics of the practical use of the system, where user generally positions the optical system such that the object of interest is in the center of the field. Based on the satisfying performance demonstrated by the MTF curves of FIG. 8, the proposed design is operationally sound at least in the visible portion of the optical spectrum.

TABLE 2

Refractive Indices for materials of optical elements of Table 1:

| MATERIAL CODE | WAVELENGTHS | | |
|---|---|---|---|
| | 600.00 | 562.50 | 525.00 |
| NSK16_SCHOTT | 1.619768 | 1.621829 | 1.624331 |
| NFK5_SCHOTT | 1.487054 | 1.488449 | 1.490126 |
| NLAF2_SCHOTT | 1.742950 | 1.746246 | 1.750303 |

TABLE 2-continued

Refractive Indices for materials of optical elements of Table 1:

| MATERIAL CODE | WAVELENGTHS | | |
|---|---|---|---|
| NBASF64_SCHOTT | 1.702905 | 1.706442 | 1.710819 |
| ACRYLIC | 1.491227 | 1.492930 | 1.495024 |

| MATERIAL CODE | WAVELENGTHS | |
|---|---|---|
| | 487.50 | 450.00 |
| NSK16_SCHOTT | 1.627429 | 1.631356 |
| NFK5_SCHOTT | 1.492185 | 1.494774 |
| NLAF2_SCHOTT | 1.755407 | 1.761994 |
| NBASF64_SCHOTT | 1.716362 | 1.723582 |
| ACRYLIC | 1.497652 | 1.501027 |

The skilled artisan having the advantage of knowing the example of design of the optical system utilized in an embodiment of the invention, will now readily appreciate that the optical system includes an optical lens having an optical axis and a front lens element (having a non-zero optical power) that faces the encapsulating optically-transparent shell. The front lens has an apex at the optical axis. The optical lens is mounted within the shell such as to be rotatable about an axis of rotation at a rotation angle that is defined between the shell axis and the optical axis and that can assume each and every value within a range from at least −90° and +90° in a chosen plane that contains both the shell axis and the optical axis. Preferably, the encapsulating shell is configured as a first optical imaging element of the camera itself, dimensioned as a substantially-spherical shell having a shell axis. In this example, it is the combination of the substantially-spherical first optical imaging element with the optical lens enclosed by such first optical imaging element that is required to form, define, and be identified as the optical imaging system. In the specific example discussed above the optical lens has a field-of-view (FOV) with a semi-angle of up to 88° as measured with respect to the optical axis of the optical lens, but since a skilled artisan will now recognize how to change the value of this FOV, there is simply no practical reason to present an alternative, related example of the optical system.

Example(s) of Optoelectronic and/or Optoelectromechanical Sub-Systems.

Now, several related and/or alternative but, nevertheless non-mutually0 exclosure examples of operable cooperation between the optical system and additional opto-electronic components and a lens housing structure, which gives rise to an optoelectronic system of an embodiment of the invention, are discussed.

Example A

Figure 11:
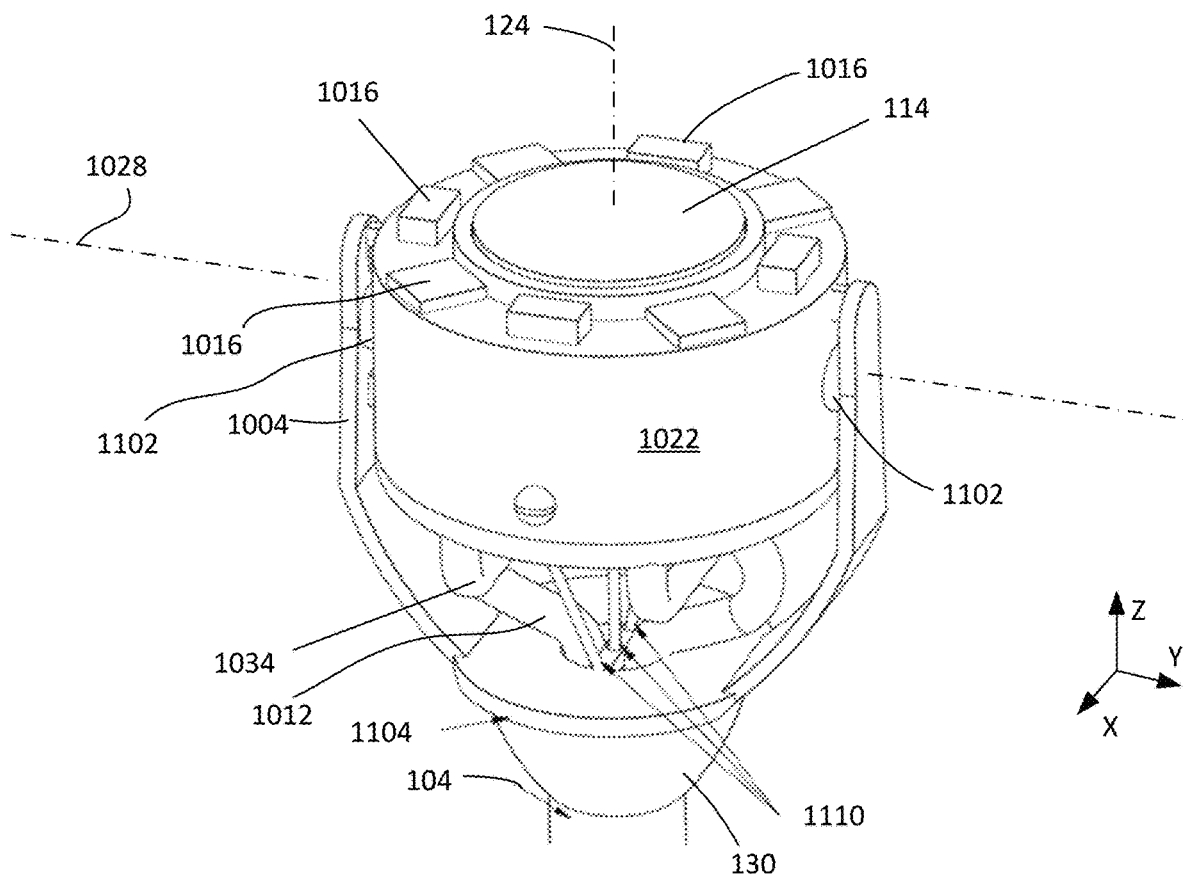
FIG. 11 provides a perspective a view of the embodiment corresponding to FIGS. 10A, 10B but without the outer housing shell to show positions of cords, electrical wires and base plate.

An example 1000 of the embodiment 100 is schematically illustrated in two side views of FIGS. 10A and 10B, in which the optical lens 114 and the shell 120 are shown in their nominal mutual orientations. FIG. 11 illustrates the example 1000 without the housing shell 120 in perspective view. The individual elements/lenslets of the lens 114 are housed in corresponding lens-holder(s) or housing 1004 (corresponding to 118 of FIG. 1 and made from, for example, aluminum-alloy) that are structured to include appropriate apertures and/or spacers and/or spatial extension to block stray light. The components of the lens-holder 1004 can also be made of plastic or other materials. In one implementation, the lens 114 and its housing 1004 have an overall length of about 5 mm to 6 mm, with an outer diameter of about 4 mm. Image sensor(s) (optical detector(s), not shown, are mounted on a Printed Circuit Board (PCB) 1008 that may be attached to the base of the lens holder 1004. In FIGS. 10A, 10B the lead-line from the numeral 1008 point to both the image sensor PCB enclosure and appropriately-dimensioned slots for electrical members 1012 (for example, wires) leading to the PCB. For illumination, light emitting diodes (LEDs) 1016 are mounted around the lens 114 and preferably at the front of the lens housing 1004. The set of LED sources 1016 are chosen and appropriately configured to provide preferably spatially-uniform illumination/irradiation of the target object space through the shell 120 with white light and/or mono-chromatic light and/or electro-magnetic radiation at non-visible wavelengths.

An image sensor or optical detector is, understandably, positioned behind the lens 114 at the image plane to capture the image through the shell 120 and the optical lens 114. As the embodiment (100, 1000) is powered externally and image transmitted via the tether 104 without the need for a battery inside the shell 120, there remains sufficient space inside the shell 120 to accommodate an image sensor that is large enough to capture images with an array of pixels containing pixels in numbers comparable to or greater than that used in traditionally-configured endoscopes and far greater than that would be possible in wireless capsulated imaging cameras. The image sensor (optical detector) is mounted on a PCB 1008 with other electronic components, thereby forming an image sensor PCB module. The detector is preferably about 5 mm in a maximum dimension to facilitate high-resolution imaging and to allow it to be easily accommodated in the shell 120.

In one specific example, there may be—incorporated in the image sensor PCB module—a Mobile Industry Processor Interface (MIPI) to Universal Serial Bus (USB) converter, a stream encoder electronic circuitry, a clock generator electronic circuitry, a microcontroller, and a variable resistor. MIPI to USB converter circuitry and the microcontroller may be configured to convert Camera Serial Interface (CSI) MIPI signals to USB transmission data. This configuration may facilitate operating the detection of the camera as a USB camera by operational systems such as Windows or Linux, for example, and load the Human Interface Devices (HID) driver to control and communicate with the camera. The microcontroller may be additionally configured or programmed to operate in coordination with the stream encoder and/or clock generator electronic circuitries to apply different stream formats based on user's selection (for example, a Motion-Joint Photographic Expert Group (MJPEG)). A variable resistor may be used to adjust the voltage applied to the LED sources to adjust the brightness of the LEDs seamlessly. It is appreciated that, as portion of the present electronics, there may be tangible non-transient memory storage with program code stored therein that, when utilized, allows the user to select different resolutions for the video stream and also grab a specific video frame and save it as, for example, a JPEG file.

The camera housing 1004 is held between two stands or arms 1022 (corresponding to 122 of FIG. 1) that are attached to the base plate (or, base of the camera stand) 1026. The stands are positioned and shaped to allow free movement of the lens housing at least bout the axis of rotation 1028 passing through the stands 1022 and lying in the plane 1030 that is substantially perpendicular to the optical axis 128. The camera is moveably affixed to the stands 1022 with appropriate axle (shown as 1102 in FIG. 11) that facilitates the rotation or tilt of the camera about or with respect to the axis of rotation 1028 (the Y-axis of the local system of coordinates, as illustrated). In one specific example, the structural cooperation between the lens holder/camera housing 1004 and the stands 1022 is judiciously configured to allow the camera to rotate freely on the axis 1028 within the range of tilt or rotation angles of +/−90° with respect to the nominal orientation shown in FIGS. 10A, 10B, 11, or even within the range of +/−180° with respect to such nominal orientation.

In at least one embodiment, the base plate 1026 may be attached and fixed to the base or lower portion of the capsule shell above and below to a strain-relief 1040 (corresponding to 130 of FIG. 1) that may be additionally secured to the outer cover or tubing of the flexible tether 104 with adhesive such as epoxy 1038, for example. The base plate 1026 may be equipped with apertures or openings 1110 (FIG. 11) through which the electrically-conducting members (shown as electrical wires, in this non-limiting example) 1012 and/or traction cords (or strings) 1034 pass. As will be explained below in more detail in reference to FIGS. 12 and 13, the embodiment 100, 1000 is configured to utilize the traction cords 1034 attached to the lens holder 1004 internally, as well as the motor control unit for changing the spatial orientation of the lens 114 with respect to the axis 124 of the embodiment. (While in one embodiment three traction cords may be used—for example, 1034A, 1034B, and 1034C—in FIGS. 10A, 10B these cords are all denoted s 1034 for the simplicity of illustration.)

The electric wires that power various components and/or sub-systems of the camera such as LEDs, for example, and that transmit the image signals emerge from the base 1026 of the capsule housing. The electrical wires exit the housing at its base and may be split in two or more bundles (<1.5 mm in diameter each) that are directed laterally, sideways through lateral slots below the housing to keep the wires away from the traction cords 1034 and to facilitate movement of the housing. To this end, the outer electrically-conducting members/wires 1012 may be passed through corresponding apertures or holes the axes of which—in at least one case—may be angled or tilted with respect to the axis 124 to spatially divert the members 1012 to opposite sides of the capsule housing, as seen in FIG. 11, for example. (The holes through which the wires exit the base plate generally have sufficient room to allow movement of the wires, to reduce the need for the wires to bend and facilitate the rotational movement discussed elsewhere. These holes/slots are structured to divert the electrical wires away from the center so that the wires mostly slide in these slots/holes as the lens 114 in the holder 1004 is tilted/rotated, while the bending of the wires is reduced—the bending, otherwise, would produce stiffness and resistance to movement—if the wires are positioned perpendicular to the axis of rotation. There is also some room around the opening of the wires at the base-plate to allow some lateral movement, again to prevent bending of electrical wires and their breaking.) In a related case, the wires 1012 can also be left unsplit/undivided from one another to form a single wire bundle or column that passes through on one side of the capsulated embodiment. The intra-capsular wires are dimensioned to be long enough to allow the camera housing 1004 to gently tilt on its axis of rotation 1028 without excessive stress on the wires 1012 and wire-related electrical connections.

In yet another related embodiment (not shown), the wires 1012 exiting the base 1026 of the housing can be wrapped around the axle 1102 of the housing structure 1026 at one or both sides so that as the housing rotates on the axle 1102 (about the axis 1028), the wires around the axle unwind or wind according to the direction of rotation movement to not subject segment(s) of wire(s) between the axle and the housing structure to tension or stress that may damage, break or disconnect the wires. In yet another related embodiment, the wires between the PCB and the tether can be replaced by a flex-circuit that can bend repeatedly without breaking.

Non-Limiting Embodiments of Various Controllers for Use with System(s) of Example A.

Figure 12:
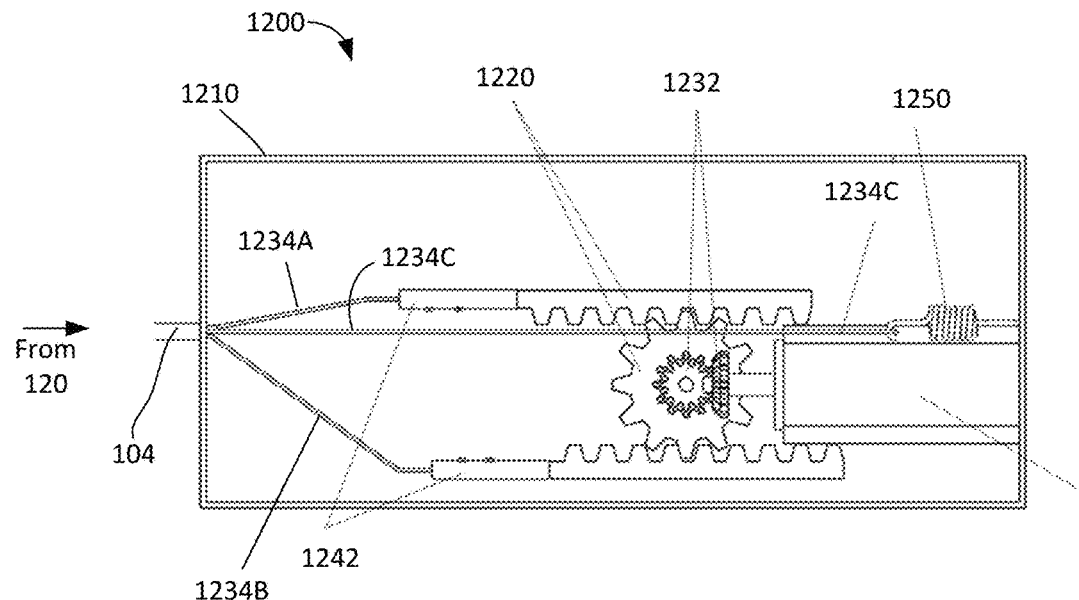
FIG. 12 is a schematic diagram of a hand-held remote controller equipped with a motor. The optionally present electronic circuitry and/or microcontroller configured to govern and operationally-cooperated with optoelectronic components and/or subsystems of the embodiment of FIGS. 10A, 10B are not shown for simplicity of illustration.

FIG. 12 provides a schematic illustration of a non-limiting example of a controller 1200 of a hand-held unit (or, remote controller) equipped with a motor that can be used in conjunction with the embodiment of an optoelectromechanical system such as that of FIGS. 10A, 10B, 11 to effectuate the rotation of the camera of the embodiment (and with it, the imaging lens 114) about the axis of rotation 1028 within the bounds of the substantially-spherical optical shell 120 while keeping the shell 120 substantially immobilized with respect to the tether 104. Notably, only the mechanical driver portion of the remote controller is shown for simplicity of illustration, thereby excluding the showing of various electrical wiring such as members 1012, for example, as well as microcontrollers and/or programmable electronic circuitry that may be arranged to be external to the embodiment 100, 1000. The remote controller 1200 depicted in FIG. 12 includes, enclosed in an appropriately-dimensioned housing 1210, a rack-and-pinion mechanism 1220 configured to drive/pull the camera-tilting/driving flexible traction cords 1234(A,B,C) (corresponding to the cords 1034 of FIGS. 10A, 10B) with the use of the DC/stepper motor 1238 in order to transfer the pulling motion applied to the cords to the rotational movement of the lens 114 about the axis of rotation 1028. The force and torque generated by the motor 1238 is transferred to the rack-and-pinion mechanism 1220 with the use of the appropriately-configured bevel-gear mechanism 1232.

In the example of FIG. 12, shown are three traction cords 1234A, 1234B, and 1234C. In further reference to FIGS. 10A, 10B, and 11, in the most general implementation all three cords 1234A, 1234B, 1234C may be disposed to exit the bounds of the shell 120 of FIGS. 10A, 10B through individual ports in the base plate 1026. In this case, the apertures or openings 1110 for the outermost (lateral) cords 234A, 1234B are angled such that the cords are directed towards the outer casing 120 of the imaging camera substantially perpendicularly to the wires 1012 and stands 1022 that support the axle(s) 1102. The central cord 1234 then is placed to exit the shell 120 through its own, respectively-assigned central one of apertures 1110.

Distal ends two of the three cords—cords 1234A and 1234B—are affixed to opposite sides of the housing 1004, perpendicularly to the axis of rotation 1028, and a pulled through the respectively-corresponding apertures 1110 at the base plate 1026 of the housing 1004. The proximal ends of the cords 1234A, 1234B are cooperated with the rack element of the rack-and-pinion mechanism 1220 with the use of, in one implementation, a fishing-line type fixation element(s) 1242 utilizing set screws (it is understood that a differently configured fixations can be used as well). Through the mechanism 1220 and the mechanism 1232, these cords 1234A, 1234B are further attached to the motor 1238 (or, in a related embodiment, a hand-dial type of the repositioner placed instead of the motor 1238; not shown) that in operation provides the traction needed to move the cords within the tether 104 and hence tilt or rotation the imaging camera of the embodiment 100, 1000 in the angular space denoted as "altitude" in FIG. 1. In particular, traction applied to a chosen one of the lateral cords 1234A, 1234B with the use of the mechanisms 1232, 1220 transfers the torque generated by the motor 1238 to the rotational motion of the housing 1004 to tilt the housing 1004 (and with—the lens 114) towards and in the direction of such chosen cord. An edge of the camera housing 1004 that comes into contact with the lateral cords 1234A, 1234B (or, the respectively corresponding cords shown as 1034 in FIGS. 10A, 10B) may be spatially-curved to reduce friction experienced by the cords and the off chance that the cords may wear out during repeated pulling/tilting. As the cords 1234A, 1234B (and 1234C, if used) exit the housing of the hand-remote unit, or at points where they change direction, they will pass around rounded surfaces such as pulleys (not shown), to reduce friction when traction is applied.

A third traction cord, shown as 1234C, may be drawn between the lateral cords 1234A, 1234B and attached at its distal end to the center of the base 1026 of the camera housing to favor positioning of the camera at a 0° tilt, or at the longitudinal axis 124 of the embodiment 100, 1000. While the two lateral cords are connected to a motor 1238 at the remote controller 1200, the central cord 1234C maintains tension at a substantially constant, unchanging level by being attached proximally to a resilient element 1250 (shown as spring) in the housing 1210 of the controller 1200. In at least one case, the flexible cords 1234(A,B,C) may be made of materials such as nylon, fluorocarbon, or polyethylene, and dimensioned to be about 0.15 mm in diameter in order to withstand force/weight of at least 250 g (in a related embodiment—up to 500 g; in yet another implementation—up to 1 kg).

It is appreciated, therefore, that a combination of optoelectronic system that includes the imaging camera (providing at least a portion of the optical imaging system of an embodiment of the invention) and associated electronic components and subsystem as discussed in reference to FIGS. 10A, 10B, 11, together with the mechanical arrangements discussed in reference to FIG. 12 forms an optoelectromechanical system according to one embodiment of the idea of the invention. In such optoelectromechanical system, a first string is connected to a first point of the holder of the optical lens of the embodiment and a second strings is connected to a second point of the holder of the optical lens (with the first and second points being substantially diametrically opposed to one another with respect to the optical axis of the optical lens). The first and second strings are drawn through the tether of the embodiment to a remote controller at the second end of the tether, and the remote controller is configured to have a chosen one from the first and second strings pulled to tilt the optical lens with respect to the axis of the substantially spherical shell of the embodiment.

Depending on the specifics of a particular implementation of the optoelectromechanical system of the invention, at least one of the following conditions may be satisfied: (a) the optoelectromechanical system includes a third string connected to a center of the base portion of the holder of the optical lens and drawn through the tether between such center of the base portion and a resilient element within the remote controller, while the remote controller is configured to stabilize a neutral orientation of the optical lens; (b) the remote controller includes a rack-and-pinion mechanism within a housing of the remote controller, such mechanism being configured to pull a chosen one of the first and second strings; and (c) within the housing of the remote controller, there is a motor and, optionally, a microcontroller configured to govern the motor to operate the rack-and-pinion mechanism.

Figure 13:
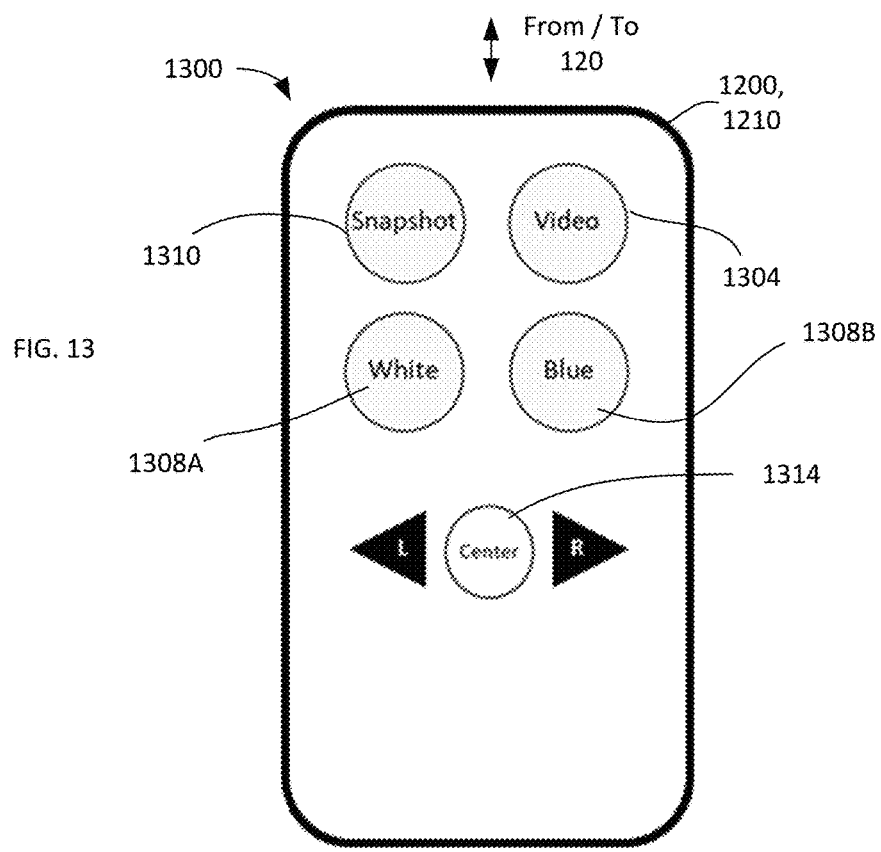
FIG. 13 provides a schematic of an example of a control panel of the hand-held remote controller.

For completeness of the description of the example, the schematic of a panel 1300 of the remoter controller 1200 is shown in FIG. 13, illustrating buttons/key and corresponding insignia on the front portion of the housing 1210. As was already alluded to above, the controller 1200 may additionally include a microcontroller (not shown) configured to facilitate delivery of electrical power and transfer of electrical signals to and from the embodiment of the optoelectronic system contained in the shell 120 through the wiring inside the tether 140, start and/or stop the imaging process, govern the operation of the illuminating light sources (controls 1308A, 1308B) delivered from the white or monochromatic LEDs 1016 through the optically-transparent shell 120 to the target portion of the object space (e.g., the internal organ of interest), and/or to format imaging process to acquire individual snapshots and/or video recordings (see controls 1310), and, for example, govern the movements of the encapsulated imaging camera (controls 1304, 1314).

In further reference to FIG. 12, while the specific implementation of the movement controller illustrated in that Figure is designed to be motorized, in a related embodiment it may be replaced with a manual dial. As shown, however, the stepmotor 1238 is used to control the position of the camera head, for example the clockwise rotation of the motor leads to rotation/tilt of the camera head in a clockwise direction (with respect to the chosen reference axis and/or plane), while the counterclockwise rotation of the motor 1238 causes the camera head to rotate/tile in a counterclockwise direction. The stepmotor may be powered via the USB3.0 connector; buttons/keys 1314 can be pressed to direct the camera to a desired direction. The adjustor "R" may be associated with rotating the camera head rotate clockwise, while the adjustor "L" can be wired to rotate camera head rotate counterclockwise. The adjustor "Center" is structured and appropriately wired to return the camera to its original, nominal position along the axis 124 of the capsular shell 120, or 0° in the "altitude" angular space of FIG. 1.

As far as the process of irradiating the object space with light from the light sources 1016 is concerned, the remote controller 1200 may have two groups of buttons/keys/adjustors to switch between white and mono-chromatic LEDs, 1016. One group (labelled 1308A) may be used to control the white-light LEDs 1016, while the other (labelled 1308B) may be used to control the monochromatic LEDs 1016 or alternate source of electromagnetic radiation present at the embodiment of the camera. The brightness of the LEDs 1016 may be controlled by changing the current to the LEDs from 0 A to 0.6 A, in one case. The "snapshot" button 130 is wired to grab the current, instantaneous image frame from the overall video stream recorded by the camera and to save such frame into the specified data folder of the tangible storage medium of the embodiment as a JPEG file. The "video" button 1304 and associated portion of the electronic circuitry of the embodiment of the remote controller 1200 may be used to record a video of the display by pressing this button.

Non-Limiting Example of a Tether for Use with System(s) of Example A.

Figure 14:
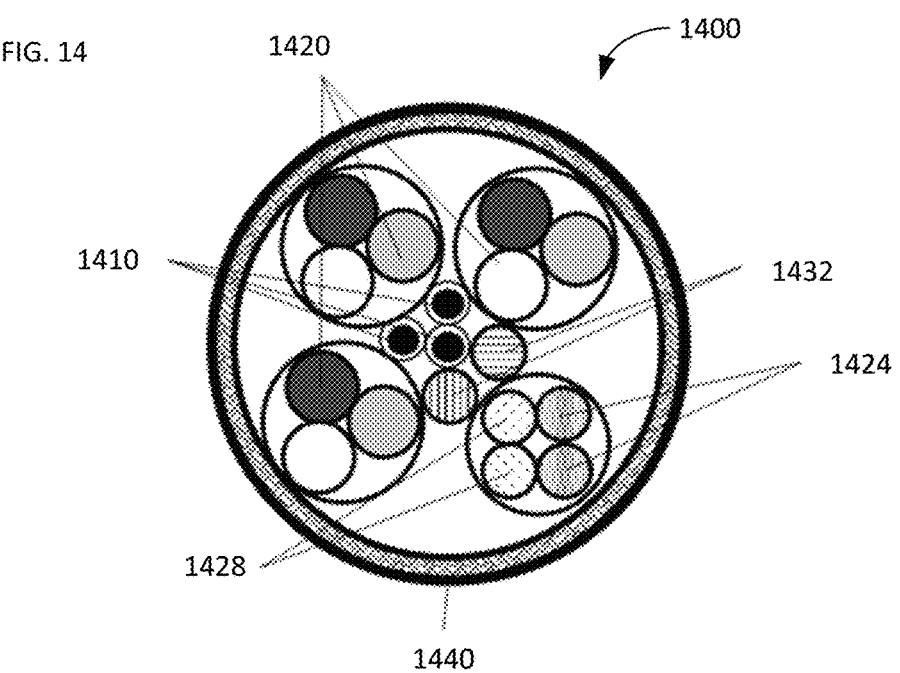
FIG. 14 illustrates schematically a cross-section of a tether with electrically-conducting members and low-friction tubes with cords/strings for traction drawn through the tether.

As a skilled artisan has readily appreciated by now, the cooperation between an imaging camera of the system of the invention and the remote controller 1200 and/or auxiliary external microcontroller and/or programmable electronic circuitry (which, when present, is indicated with the arrow in FIG. 1) is provided with the use of the tether 104 that is devoid of any channel configured to transmit light. To this end—and in reference to FIG. 14 showing a schematical cross-section of an embodiment 1400 of the tether 104—once the traction cords 1234(A,B,C), for example, exit the shell 120 through the strain relief element 130, the cords are individually housed inside respective low-friction flexible tubes that facilitate the movement of the cords along and inside the tether 104, 1400 to successfully tilt the camera in the desired direction. The traction cords 1234(A,B,C) in the respectively-corresponding tubings are packaged along-side the electrical wires 1012 that are housed in their respective insulating covers inside the tether 104, 1400. In particular, FIG. 14 illustrates tilt-driving cords inside low-friction tubes as 1410, and three shielded differential electrical-member pairs with ground wires as 1420. Numeral 1424 denotes the electrical members configured to transfer serial data and clock (clocking data); numeral 1428 identifies the electrical members transferring the LED control signals; numeral 1432 represents the members configured to represent the power transfer and/or ground; while numeral 1440 identifies the PVC jacket and braid shield, when present.

In one non-limiting example, the outer diameter of an embodiment 1400 of the tether 104 may be about 3 mm; the tether is made highly pliable (for example, of polyurethane or silicone or a similar material that is in addition fluid resistant) to facilitate swallowing and using of the capsule 100, 1000 with the tether inside the gastro-intestinal tract. The outer surface of the tether 104 preferably carried markings at regular intervals along the length (for example, every 1 cm and every 5 cm) to allow the user/clinician to assess distances from the incisors and/or the entry point of an organ that is at the moment optically investigated with the camera of the embodiment, to estimate the dimension(s) of lesions or objects encountered in that organ. The tether can be made 50 cm to 100 cm in length, in at least one case, or it may be made to be longer or shorter, depending on the specific application.

Example B

Figure 16:
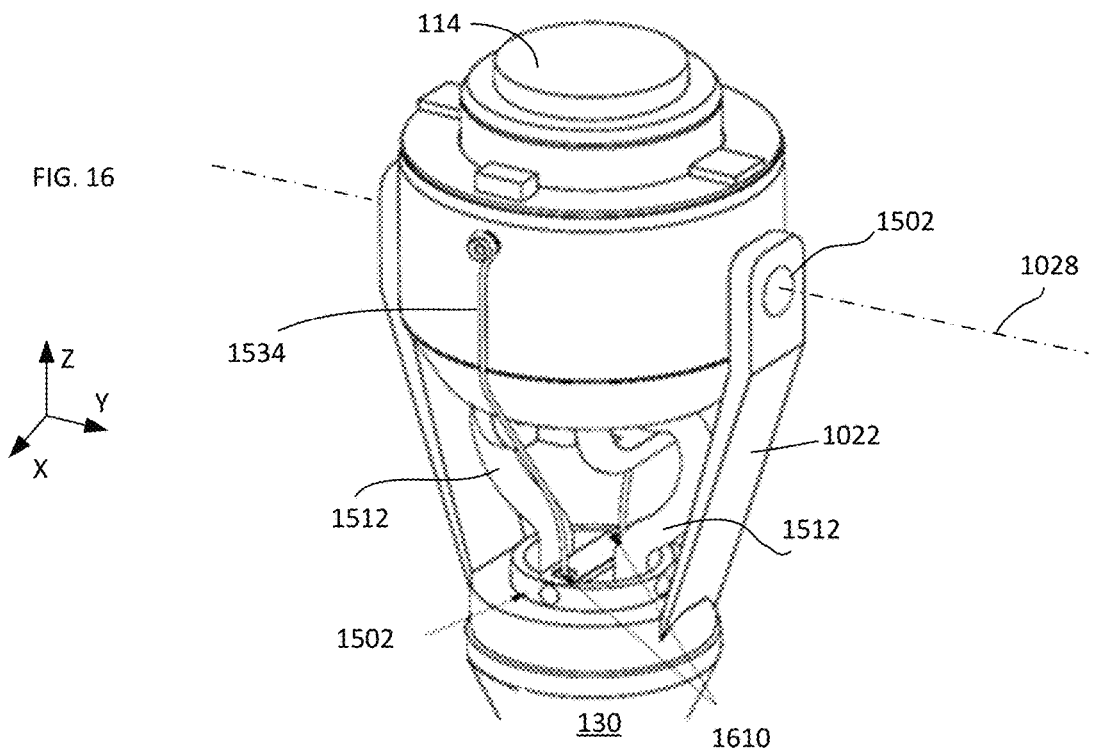
FIG. 16 provides a perspective a view of the embodiment corresponding to FIGS. 15A, 15B but without the outer housing shell to more clearly illustrate positions of cords, electrical wires and base plate.

A related embodiment 1500 of the optoelectronic/optoelectromechanical encapsulated system of the invention (approximately corresponding to that displayed in FIG. 2) is schematically illustrated in FIGS. 15A, 15B, 16. Being generally very similar to that of the embodiment discussed above in reference to FIGS. 10A, 10B, 11, the housing structure (including at least the lens holder 1504, the stands or arms 1022, the axle(s) 1502 defining the axis of rotation 1028 and with respect to which the lens 114 with the lens holder 1504 (with the associated enclosed PCB and the image sensor 1508) can be tilted or rotated and that connect the stands 1022 with the lens holder 1504) inside the substantially-spherical shell 120 may nevertheless be configured a bit differently from the housing structure of the embodiment 1000 to accommodate the differences in electrical wiring 1512 and tilt/driving string 1534 cooperation from those of the embodiment 1000.

In particular, the electrical wiring 1512, which power the imaging camera, LEDs 1016, and that transmit the signal representing an acquired optical image(s) through the tether 104, emerge from the tether at base 1526 of the housing structure and then may be split in two or more wiring bundles that are optionally directed laterally through appropriately-dimensioned lateral slots 1530 below the housing to keep the individual bundles away (spatially separated) from the two cords 1534. The wires 1512 can also be configured to form a single column or bundle that passes through on one side of the encapsulated optoelectronic system. In any case, the portion of the electrical wiring within the shell 120 is long enough to allow the imaging camera to gently tilt about the axis 1028 without excessive stress on the wires and their connections. There are two traction cords 1534 in this implementation, that are drawn through respectively-corresponding openings 1610 in the base plate 1526 of the housing structure (see FIG. 16). The ends of the cords 1534 are attached to the opposite sides of the lens holder 1504 externally, as shown. (In comparison with the embodiment 1000, the third, centrally-located cord is optional and not present in the illustrated case but, if present, can be used to help position the camera in the forward or 0° position, with its own drive motor or spring in the hand-control unit, as discussed above in reference to the embodiments 1000, 1200.) Just as in the embodiment 100, the flexible cords 1534 can be made of materials such as nylon, fluorocarbon, or polyethylene; be about 0.15 mm in diameter, able to withstand weights to facilitate camera movements; as an example, a flexible cord able to withstand repeated traction weight of about 250 mg or more (preferably, about 0.5 kg or more, and in a related case at least 250 g) to be used to repeatedly tilt or rotate the camera housing about the rotation axis 1028 defined by the axles 1602. Two cords are attached to opposite sides of the housing, substantially perpendicular to the axis of rotation and pass-through holes at the base plate to which the frame is attached. Tension on a lateral cord 1534 through the tether 104 tilts the lens holder 1504 in the direction of such cord. Subsequent tension on the other traction cord 1534 tilts the holder 1504 in the opposite direction. The edge of the camera housing/holder 1504 that comes into contact with the lateral cords is preferably curved to avoid a sharp edge and thus reduce friction and the chance of the cords breaking from repeated tilting (FIGS. 15A, 15B, 16).

The light sources 1016 and the imaging modes of operation of the embodiment 1500 are substantially the same as those of the embodiment 1000.

In particular, the brightness of the LEDs 1016 may be adjusted with the use of an appropriate program code with which the microprocessor of the embodiment is loaded, which code continuously samples intensity of an acquired optical image. The program code may be configured to additionally or in the alternative vary and optimize image contrast. The illumination delivered from LEDs 1016 through the optically-transparent portions of the substantially-spherical shell 120 can be continuous or pulsed. The modality in which the current through the LEDs 1016 is varied has the advantage of facilitating the delivery of higher-level currents to the LEDs to produce pulses of illuminating light, while at the same time avoiding problems of overheating of the embodiment as compared to the case of using continuous current required for a temporally-continuous illumination of the object space. Pulsed lighting will also generate a higher intensity of light, thereby enabling the illumination of portions of the object space not reached with a lower intensity continuous beam. With more than one color of light from the LEDs 1534 (such as white and blue light, for example, both of which can be alternately pulsed) imaging can be configured in a color-interleaved fashion, for example, when illumination of the object space in only one specific color selected at a time light can be selected as desired. With three (or more) types of LED illumination, such as white, cyan and infra-red, all three (or more) can be sequentially pulsed to provide three (or more) imaging modalities, as a person of skill in the art will readily appreciate. Finally, more than one type of illumination can be combined to provide a blended image with, e.g., white and cyan illumination, with infra-red superimposed on it, to provide information about tissue characteristics, such as vascularity and metabolism.

Furthermore, just as in the case of the embodiment 1000, whereas white light LEDs 1534 may be used for most inspections of biological or inanimate structures of the object space through the shell 120, additional lighting can be used for selective imaging, such as the use of monochromatic light to display high contrast images. As an example, blue or cyan light can be used to provide high contrast images to display vasculature as well as changes in cellular lining of a biological organ, such as differences between squamous and columnar mucosa. In addition, wavelengths outside the visible spectrum can be utilized, such as Ultra-Violet or Infra-Red to display images. Electro-magnetic wavelengths may be used to excite molecules in the tissues or materials surrounding the capsule to generate fluorescence images that provide additional images or data characteristic of diseases or conditions such as cancer or inflammation or metaplasia. A plurality of optical techniques from white light imaging, to monochromatic light imaging to fluorescence, absorption, and multi-photon imaging may be incorporated into such a tethered capsule, as well as methods used to image the structure of surrounding materials and tissues, such as ultrasound or photo-acoustic imaging.

Figure 17:
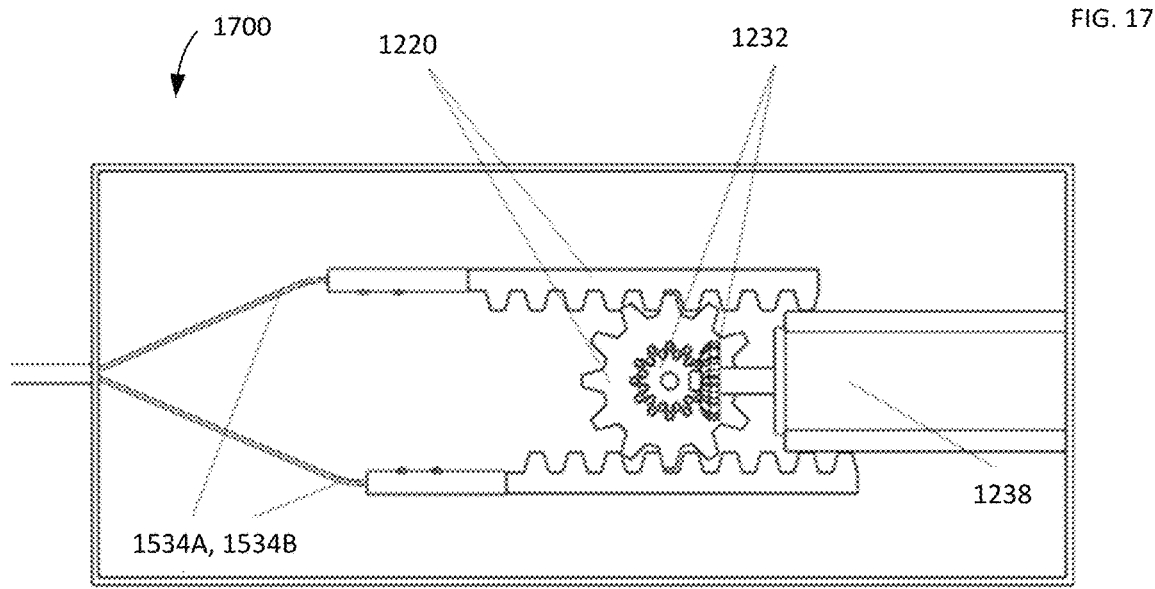
FIG. 17 contains a schematic diagram of a hand-held remote controller equipped with a motor, configured for use with the embodiment of FIGS. 15A, 15B, 16. The optionally present electronic circuitry and/or microcontroller configured to govern and operationally-cooperated with optoelectronic components and/or subsystems of the embodiment of FIGS. 10A, 10B are not shown for simplicity of illustration.

The schematic of the hand-held remote control unit 1700 of the embodiment 1500 is illustrated in FIG. 17: it is substantially similar to that of FIG. 12, with the exception that operation of only two tilt cords (1534A, 1534B) should be governed in the latter case. (If and when the optional third cords 1534C is also used, the embodiment of FIG. 12 can be employed.) The cords may be passed around curved surfaces or pulleys (not shown) to minimize friction.

The cooperation between an imaging camera of the system 1500 and the remote controller 1700 and/or auxiliary external microcontroller and/or programmable electronic circuitry (which, when present, is indicated with the arrow in FIG. 1) is provided with the use of the tether 104 that is devoid of any channel configured to transmit light. To this end, and in reference to FIG. 18, shown is a schematical cross-section of an embodiment 1800 of the tether 104 that may include an envelope or tubular member 1804 of a metallic braided shield further encased in a poly-vinyl chloride covering 1810. Once the two traction/tilt cords or strings 1534 (shown as black circles in the central portion of the schematic 1800) exit the shell 120 through the strain relief element 130, these cords are individually housed inside respective spiral coils 1814 (shown as circular boundaries around the black circles) that facilitate the movement of the cords along and inside the tether 1800 to successfully tilt the camera in the desired direction. Each traction cord exits the camera capsule through separate holes on the base plate 1526. The holes may be angled laterally to one another to contain and guide the two cords 1534 near the center of the base plate to enter the tether 1800. The coiled springs can be made of materials such as stainless steel. As an example, a nylon traction cord 0.15 mm in diameter can be encased in a stainless-steel coil of about 0.3 mm inner diameter, and about 0.5 mm outer diameter, and made from a 0.1 mm stainless-steel wire. The coiled springs allow the tether 1800 to be flexed without the coiled spring lumen collapsing or kinking. The coiled springs further allow for changes in the lengths of the traction cords 1534, and enables traction cords 1534 to move freely with minimal resistance. The coiled springs are preferably placed at the center of the tether, and are adjacent to (and/or surrounded by) electrical wires 1812 (wires for power, ground, and control signals, 1822 (this one indicating shielded differential pairs and ground wires for data transmission) so as to minimize bending or stiffening of the tether 1800 when tension is applied to a given traction cord 1534. The metallic braided shield 1804 is grounded. This avoids electro-magnetic interference with data transfer through the wires in the interior of the cable and minimizes such effects on regional organs of the body. The coiled springs 1814 can be grounded at the hand-held control unit 1700.

Example C

FIGS. 19A, 19B illustrate another related embodiment of the system of the invention (which may possibly be viewed as a structural blend of the embodiment of FIGS. 10A, 10B and that of FIGS. 15A, 15B), demonstrating that various elements and components of various related embodiments can be interchangeable. Here, the electrical wires 1912 operably connected to the electronics of the camera are shows to be directed laterally to form spiral loop(s) 1912A about the axles (fitting and resting in the openings 1920 in the stands 1022) before exiting through holes in the base plate and entering the tether through the straight relief 130. The spiral loop 1912A allows the camera to tilt repeatedly without breaking the wires. The loops 1912A may be formed on one or both axles. In this embodiment, there are shown three traction cords 1934, by analogy with the embodiment 1000, which pas through the corresponding openings 1938 and may be operated with the use of the controller 1200 through the tether configured according to the embodiment 1400, for example. Numeral 1940 denotes a base plate attachment to tether with a fitting connector and adhesive and covered with a strain relief element 130, while numeral 1942 denotes slots dimensioned to spatially divert the electrical wires away from the axis and to the sides of the embodiment 1900.

FIGS. 20A, 20B schematically (and not necessarily precisely) illustrate two different positions of a portion of the imaging system of an embodiment of the invention in which corresponding angular orientations of a portion/lens 114 (with a semi-angle of the corresponding FOV denoted as A) of the imaging system housed in a lens holder 1004, 1504 that is disposed inside the substantially-spherical shell-shaped front lens element 120 of the overall imaging system differ from one another as a result of the operations of the traction cords (1034, 1234, 1534, 1934). In particular, FIG. 20A illustrates the embodiment in a nominal angular orientation when the axis 128 of the lens 114 and the axis 124 of the shell 120 substantially coincide, while FIG. 20B illustrates the embodiment in the tilted orientation when the angular inclination between the axis of the lens 114 and the axis 124 of the shell 120 is denoted by angle B. Numeral 2004 denotes the axial and outermost rays subtending the angle A. Arrow 2010 points towards an embodiment of a tether and, through it, to a remote control. Point P is an axial point of the lens 114 at the top aperture that remains the shortest separation of which from the shell 120 remains substantially constant regardless of the variation of the tile angle B within the available range of the altitude angles (see FIG. 1). A skilled artisan will readily appreciate that, for a fixed design of the optical lens 114 such condition translates to maintaining an apex (an outermost front point) of the lens 114 to remain substantially equidistant from the inner surface of the shell 120 within which the rotation of the lens 114, the holder of the lens 114, the sources 1016, and the corresponding optical detector is carried out simultaneously.

Based on the discussed above mechanical cooperation between the first shell-like lens element and the optical lens within this first lens element, the combination of the two is made spatially-repositionable as a whole such that when the first lens element is relocated in space is a pre-determined fashion in absence of rotation of the optical lens about the axis of rotation, the optical lens is relocated in space in the same pre-determined fashion.

As follows from the above-provided description of the optical system of the invention, for an imaging camera the optical system of which is characterized by a (full-angle) FOV of about 180° (as in the example discussed above), tilting or rotating of the camera by +/−90° from the nominal mutual orientation between the shell 120 and the optical lens 114 allows the user to complete an almost 360 degree view and imaging of the object space in a plane containing the axes 124, 128 (and, if the rotation of the embodiment about the axis 124 is added by, for example, twisting the tether— an almost spherical view of the object space). This design allows, as an example, the desired and complete viewing from the pylorus to the gastro-esophageal junction of the stomach, as schematically illustrated in FIGS. 9A, 9B. If the bodily organ or other object space being imaged is tilted or bent slightly (as a result of, for example, bending the body of the patient) with respect to the axis 124, even the view of a portion of the object space that otherwise may be obscured by the tether can be successfully imaged. With rotation of the lens 114 inside the lens element 120 beyond the +/−90° range, the possible angular gap that may be present above the camera (as seen in FIGS. 9A, 9B) along the tether and not otherwise covered by the FOV of the camera gap above the capsule may be almost completely covered (thereby eliminating the "blind spot" of the camera), except possibly for the space blocked from the view by the tether and strain relief (but even this deficiency may be compensated by slight tilting or bending of the organ.

If an image is captured with the camera in the nominal orientation (that is, looking at the object space along the axis 124, forwardly) and then the lens 114 is tilted/rotated repeatedly to the left and right from the nominal orientation while accompanying such rotation with the longitudinal repositioning of the embodiment along the tubular bodily organ, a substantially complete spatially uninterrupted view of the tubular organ may therefore be obtained, including views behind folds or obstacles of the organ that would normally not be seen by a conventional forward-viewing instrument employed by related art. If necessary, stitching of various images can be performed with software to account for overlapping images, to construct a complete, continuous image of a tubular organ or pipe or intestine with folds, or cavity or space. As an example, if the tethered capsule is pulled back along the small intestine, tilting the lens 114 within the lens element 120 to the left and right allows viewing of mucosa behind the hundreds of folds (plicae circulares) in the small intestine that are not well seen by a forward-viewing enteroscope employed in related art.

Alternatively or in addition, when the optical system is configured to provide an overall semi-angle of the FOV that is smaller than 90°, the tether can be twisted so that the field within the overall, aggregate view of the imaging camera can fill in and cover he gaps in lateral view along the azimuth, while traction or release of the tether itself can be used to accomplish complete tubular, co-directional views of a tubular organ or pipe or intestine, or cavity or space.

The capability to repeatedly direct (back and forth) the imaging camera longitudinally allows a predetermined portion of the object space (such as an area of interest of a bodily organ) to be repeatedly imaged, including imaging with alternative modes of illumination discussed above, or to observe an area that may not have been seen earlier due to a muscular contraction of an organ. Further, by rotating the lens 114 at a slightly different angle, the topography of a lesion can be better assessed to aid diagnosis, such as when inspecting the outer margins of an ulcer. In further reference to FIGS. 9A, 9B, raising (repositioning) the capsule of the embodiment along the vertical axis and rotating the lens 114 upwards enables a substantially complete view of the fundus, cardia and gastro-esophageal junction of the stomach. The combination of views provide an almost completely spherical view of an organ such as the stomach.

Collected images can be further displayed and computer-vision processed with artificial intelligence systems used to provide automated lesion identification and localization without and within co-directional images. The advantage of such a display and relation between images is that it prevents disorientation of the observer when camera(s) are moving in varied directions and allows camera movement to be controlled by feedback from the imaged displayed with reference to the selected reference image. As an example, if the standard image is that of the pylorus of the stomach, other images can be displayed with reference to the pylorus such that images of the lesser or greater curvature, or the anterior of posterior walls of the body of the stomach will be immediately known by the physician; this will allow more accurate and correct localization of a lesion in the stomach.

It is understood, therefore, that in accordance with the idea of the invention, an encapsulated and tethered imaging camera and a method for operating such camera are provided.

Generally, a version of the camera as discussed here contains an internal (substantially encapsulated in a non-zero optical power optically-transparent substantially-spherical shell-like lens element) lens assembly, an image sensor or optical detector, light emitting diode(s) configured for illumination of the objects space through this shell-shaped outer casing, which internal lens assembly is positioned such that it remains substantially equidistant from the shell at all its positions for viewing. In one example, the internal lens assembly includes four elements providing for a FOV that subtends substantially 180° while keeping the spatial resolution of imaging of about 50 μm. The wider the angle of view, the wider the space that can be imaged at any one time, however, the angle of view may be varied according to the needs of an application. The constituent lens elements can be of plastic polymers or can be made of glass. For use in the esophagus and stomach, the optics are designed to provide optimum imaging performance over the range of distances expected in the esophagus and upper stomach from the surface of the capsule to 10 cm or further. The focal lengths and focusing distances can be varied according to the needs of the capsule. In related implementation, the lens can have a fixed focus, or have auto-focus capability, or may include a liquid lens to enable re-focusing. The lens design understandably accommodates the refractive index of the transparent casing of the capsule so that there is no image distortion as the internal lens assembly is angularly re-oriented in the altitude angular space.

A method for using such imaging camera generally includes illuminating a target portion of the object space through the first optical element with light generated by the light sources inside the first optical element and forming an optical conjugate of a spatial distribution of the light, which has been reflected by the target portion, at the optical detector by transmitting said light through the optical imaging system. A method may also include a step of moving the optical lens inside the substantially-spherical shell of the camera while keeping the shell fixed with respect to the target portion and/or one of: —repositioning of the substan-tially-spherical shell with respect to the target portion while keeping the optical lens immovable within the shell; and— repositioning of the substantially-spherical shell with respect to the target portion while moving the optical lens inside the shell. Alternatively or in addition, an embodiment of the method may include transferring electrical signals representing said optical image from inside the substantially-spherical shell to electronic circuitry located outside the shell along the tether and at least one of: —passing along the tether an electrical signal that defines a stream format for the transferring of the optical images, and—with the use of a microcontroller, adjusting voltage applied to the light sources of the optical imaging system to vary intensity of light generated by at least one of said light sources. In substantially any implementation of the method, at least one of the following optional conditions may be satisfied: —the process of transferring of electrical signals includes transferring electrical signals along an electrically-conducting member that passes through an opening formed in a base of a holder of the optical lens, wherein said opening is dimensioned to not constrain a movement of the member in the opening when a portion of the optoelectronic system to which the electrical member is connected is being tilted or rotated; —said transferring includes transferring electrical signal along the electrically-conducting member that is positioned to form a loop or a spiral around an axle of rotation of the optoelectronic system to reduce bending of said member when the portion of the optoelectronic system to which the electrical member is connected is being tilted or rotated; and—the opening in the base of a holder of the optical lens is dimensioned to divert the electrical member laterally away from an axis of the holder to substantially prevent bending of the electrical member when the portion of the optoelectronic system to which the electrical member is connected is being tilted or rotated. Furthermore, alternatively or in addition, the method for using the camera to form an optical image may include pulling at least one of the first string and the second string with the use of the remote controller to change an angular orientation of the optical lens with respect to the shell axis. (In at least one case, such pulling includes pulling the at least one of the first string and the second string that is covered with either a corresponding spiral coil or a tubing and located in the axial region of the tether to achieve at least one of the following effects: —to reduce a lengthening of the at least one of the first string and the second string forced by said pulling; and—to expand and contract about the at least one of the first string and the second string to reduce a degree of bending of the at least one of the first string and the second string when a portion of the optoelectromechanical system to which said at least one of the first string and the second string is attached is being tilted or rotated.) In any implementation of the method, the following operations can be performed: ceasing the pulling procedure; and manipulating the (optionally present) third string, while no stress is applied to the first string and the second string, to return the optical lens of the camera to the nominal orientation.

While specific values chosen for these embodiments may be recited, it is to be understood that, within the scope of the invention, the values of all of parameters may vary over wide ranges to suit different applications.

At least a part of the process of operation of the camera has been described as including a processor (microprocessor, electronic circuitry) controlled by instructions stored in a memory. The memory may be random access memory (RAM), read-only memory (ROM), flash memory or any other memory, or combination thereof, suitable for storing control software or other instructions and data. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

It is appreciated that the discussed opto-electronic imaging system (imaging probe) generally—and whether or not a specific configuration is expressed in the attached drawings—includes a distal portion in which an opto-electronic circuitry with an embodiment of the optical system of the invention is/are disposed, a proximal portion preferably removably connected to at least a programmable processor and/or an appropriate display device, as well as the housing or sheath (throughout which the optical and/or electrical members operably connecting the programmable processor with the opto-electronic circuitry.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes. Other specific examples of the meaning of the terms "substantially", "about", and/or "approximately" as applied to different practical situations may have been provided elsewhere in this disclosure.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

While the invention is described through the above-described exemplary embodiments, it will be understood by those of ordinary skill in the art that modifications to, and variations of, the illustrated embodiments may be made without departing from the inventive concepts disclosed herein. The disclosed aspects may be combined in ways not listed above. Accordingly, the invention should not be viewed as being limited to the disclosed embodiment(s).

What is claimed is:

1. An imaging camera having an optical field of view (FOV) and comprising:
   a first lens element having a non-zero optical power;
   an optical lens disposed inside a volume and substantially surrounded by the first lens element, wherein the FOV is defined by both the first lens element and the optical lens;
   an optical lens holder affixing constituent lens elements of the optical lens with respect to one another; and
   a first cord drawn through an aperture formed by the first lens element into the volume and attached, at an end of the first cord, to the optical lens holder.

2. An imaging camera according to claim 1, wherein:
   the first lens element is dimensioned as a substantially spherical shell having a shell axis;
   the optical lens has an optical axis and a front lens element that faces the first lens element;
   wherein the optical lens is mounted within the first lens element such as to be rotatable about an axis of rotation at a rotation angle that is defined between the shell axis and the optical axis.

3. An imaging camera according to claim 2, further comprising:
   an optical detector behind the optical lens and defining an imaging plane; and
   light sources positioned around the front lens element in a plane that is transverse to the optical axis to emit light along the optical axis,
   wherein both the optical detector and the light sources are spatially cooperated with the optical lens such as to move in spatial conformity with the optical lens.

4. An imaging camera according to claim 1,
   wherein the FOV is defined only by a combination of the first lens element and the optical lens, and
   wherein the imaging camera further comprises a light source located inside the volume and an electrical member drawn through the aperture into the volume and electrically connected to the light source.

5. An imaging camera according to claim 1, further comprising:
   a light source disposed inside the volume and configured to illuminate an object space outside the first lens element only through the first lens element; and
   an optical detector configured inside the volume to acquire light from the object space through both the first lens element and through the optical lens.

6. An imaging camera according to claim 5,
wherein the optical lens, the light source, and the optical detector are mechanically cooperated with each other with the use of a mechanical structure to form a sub-assembly in which mutual spatial positions and orientations between the optical lens, the light source, and the optical detector are maintained unchangeable; and
wherein the mechanical structure is located completely inside the volume.

7. An imaging camera according to claim 5, comprising an electrically-conducting member electrically connected to at least one of the light source and the optical detector,
wherein said electrically-conducting member is drawn through the aperture into the volume and through an opening formed in a base of the mechanical structure,
wherein at least one of the following conditions is satisfied:
(a) said opening is dimensioned to not constrain a movement of the electrically-conducting member in the opening when the mechanical structure is being tilted or rotated in the volume;
(b) the electrically-conducting member is positioned to form a loop or a spiral around an axle of rotation of the mechanical structure to reduce bending of said electrically-conducting member when the mechanical structure is being tilted or rotated in the volume; and
(c) said opening is dimensioned to divert the electrically-conducting member laterally away from an axis of the mechanical structure when the mechanical structure is being tilted or rotated to substantially prevent bending of the electrically-conducting member.

8. An imaging camera according to claim 1, wherein the aperture subtends an angle not exceeding 45 degrees as viewed from a center of a curvature of the first lens element.

9. An imaging camera according to claim 1, configured to have the optical lens rotate about an axis of rotation such that a distance separating the optical lens from a surface of the first lens element remains substantially constant for every angle of such rotation,
wherein the axis of rotation is located within the volume.

10. An imaging camera according to claim 1,
wherein the optical lens is disposed inside the volume such as to be rotatable about an axis of rotation at a rotation angle, that is defined between an axis of the first lens element and an optical axis of the optical lens and that can assume each and every value within a range from at least −90° to at least +90° in a chosen plane containing both an axis of the first lens element and the optical axis.

11. An imaging camera according to claim 1, wherein said FOV is defined by a combination of
(i) three meniscus lens elements, and
(ii) two lens elements each of which is bound by two convex surfaces.

12. An imaging camera according to claim 1, further comprising a tether having said first cord extending therethrough, wherein said tether is devoid of an optical element inside the tether, and wherein the first cord is housed in a tubing or a spiral coil disposed in an axial portion of the tether.

13. An imaging camera according to claim 1,
wherein the optical lens includes a pair of negative meniscus optical lens elements and a pair of positive lens elements, and
wherein said optical lens possesses optical distortion that does not exceed 40% at every semi-field angle up to 66°.

14. An imaging camera according to claim 1,
wherein the optical lens has an optical axis and a front lens element that faces the first lens element, and
wherein at least one of the following conditions is satisfied:
(a) a distance between an imaging plane of the imaging camera and an apex of the front lens element does not exceed 5 mm;
(b) a diameter of the front lens element does not exceed 4 mm; and
(c) a spatial resolution of the imaging camera is at least 50 microns.

15. An imaging camera according to claim 1,
wherein the optical lens holder has a front portion and a base portion, wherein the front portion carries light sources thereon;
wherein the base portion is attached to a printed circuit board carrying electronic circuitry thereon, the electronic circuitry containing a programmable microprocessor that is configured to govern an identified portion of the electronic circuitry to at least (a) define stream format for transfer of optical images, which have been acquired with the imaging camera, outside of the first lens element, and (b) to adjust a voltage applied to a light source of a plurality of light sources of the imaging camera.

16. An imaging camera according to claim 15,
wherein the first cord is connected to a first point of the optical lens holder; and
further comprising a second cord connected to a second point of the optical lens holder such that the first and second points are substantially diametrically opposed to one another with respect to an optical axis of the optical lens,
wherein the first cord and the second cord are drawn through a tether to a remote controller at the second end of the tether,
wherein remote controller is structured to pull a chosen one from the first and second cord to tilt the optical lens inside the volume with respect to an axis of the first lens element.

17. An imaging camera according to claim 15,
comprising a tether
(17a) that is devoid of an optical element inside the tether,
(17b) that contains an electrically-conducting member drawn through the aperture into the volume and electrically connected to the light sources, and
(17c) that contains the first cord and an additional cord drawn through the tether and connected to a remote controller.

18. An imaging camera according to claim 15, comprising an auxiliary cord connected to a center of the base portion and drawn through a tether between the center of the base portion and a remote controller at an end of the tether, wherein the remote controller is configured to stabilize a nominal orientation of the optical lens, and wherein the tether is devoid of an optical element within the tether.

19. An imaging camera according to claim 15, comprising a remote controller that includes a rack-and-pinion mechanism within a housing of the remote controller and configured to pull at least the first cord through a tether that is devoid of an optical element inside the tether.

20. An imaging camera according to claim 19, wherein the remote controller includes a motor and a microcontroller within the housing, the microcontroller configured to govern the motor to operate said rack-and-pinion mechanism.

21. An imaging camera according to claim 19, wherein the remote controller includes a pulley and a wheel and is configured to operate a movement of the optical lens via pulling on the first cord.

22. An imaging camera according to claim 15, comprising:
  a remote controller at the other end of the first cord, wherein the remote controller is configured to select an operation of a chosen light source of the plurality of light sources, and
  an image sensor configured to acquire an image in cooperation with the chosen light source.

23. An imaging camera according to claim 15, further comprising a tether having said first cord extending therethrough, and a second cord drawn through said aperture and said tether, wherein at least one of the first and second cords is housed in the tether at either a peripheral region of the tether or an axial region of the tether.

* * * * *